United States Patent
Josiah et al.

(10) Patent No.: US 9,957,324 B2
(45) Date of Patent: May 1, 2018

(54) ANTI-FLT-1 ANTIBODIES IN TREATING DUCHENNE MUSCULAR DYSTROPHY

(71) Applicants: SHIRE HUMAN GENETIC THERAPIES, INC., Lexington, MA (US); REGENTS OF THE UNIVERSITY OF MINNESOTA, Minneapolis, MN (US)

(72) Inventors: Serene Josiah, Lexington, MA (US); Thomas M. Luby, Lexington, MA (US); Atsushi Asakura, Minneapolis, MN (US); Dennis Keefe, Lexington, MA (US); Lawrence Charnas, Natick, MA (US); Mayank Verma, Minneapolis, MN (US)

(73) Assignees: Shire Human Genetic Therapies, Inc., Lexington, MA (US); Regents of the University of Minnesota, Minneapolis, MN (US)

(*) Notice: Subject to any disclaimer, the term of this patent is extended or adjusted under 35 U.S.C. 154(b) by 163 days.

(21) Appl. No.: 14/763,881

(22) PCT Filed: Jan. 28, 2014

(86) PCT No.: PCT/US2014/013402
§ 371 (c)(1),
(2) Date: Jul. 28, 2015

(87) PCT Pub. No.: WO2014/117160
PCT Pub. Date: Jul. 31, 2014

(65) Prior Publication Data
US 2015/0361174 A1 Dec. 17, 2015

Related U.S. Application Data

(60) Provisional application No. 61/757,571, filed on Jan. 28, 2013.

(51) Int. Cl.
*C07K 16/28* (2006.01)
*A61K 39/00* (2006.01)

(52) U.S. Cl.
CPC ...... *C07K 16/2863* (2013.01); *C07K 16/2866* (2013.01); *A61K 2039/505* (2013.01); *C07K 2317/33* (2013.01); *C07K 2317/54* (2013.01); *C07K 2317/55* (2013.01); *C07K 2317/76* (2013.01)

(58) Field of Classification Search
CPC ............ C07K 16/2863; C07K 2317/55; C07K 2317/54; C07K 2317/33; C07K 2317/76; A61K 2039/505
See application file for complete search history.

(56) References Cited

FOREIGN PATENT DOCUMENTS

WO    WO 2006/055809 A2    5/2006

OTHER PUBLICATIONS

Ennen, J. P., et al., "Vascular-targeted therapies for Duchenne muscular dystrophy", Skeletal Muscle, vol. 3, No. 1, Apr. 23, 2013, (Apr. 23, 2013), p. 9.
Messina, S., et al., "VEGF overexpression via adeno-associated virus gene transfer promotes skeletal muscle regeneration and enhances muscle function in mdx mice", The FASEB Journal, vol. 21, No. 13, Nov. 1, 2007 (Nov. 1, 2007), pp. 3737-3746.
Sanz, L., et al., "Antibodies and gene therapy: teaching old 'magic bullets' new tricks", Trends in Immunology, vol. 25, No. 2, Feb. 1, 2004 (Feb. 1, 2004), pp. 85-91.
Shimizu-Motohashi, Y, et al., "Angiogenesis as a novel therapeutic strategy for Duchenne muscular dystrophy through decreased ischemia and increased satellite cells", Frontiers in Physiology, vol. 5, No. 50, Jan. 27, 2014 (Jan. 27, 2014), pp. 1-17.
Verma, M., et al., "Flt-1 haploinsufficiency ameliorates muscular dystrophy phenotype by developmentally increased vasculature in mdx mice", Human Molecular Genetics, vol. 19, No. 21, Aug. 12, 2010 (Aug. 12, 2010), pp. 4145-4159.
Wu, Y., et al., "Anti-Vascular Endothelial Growth Factor Receptor-1 Antagonist Antibody as a Therapeutic Agent for Cancer", Clinical Cancer Research, vol. 12, No. 21, Nov. 1, 2006 (Nov. 1, 2006), pp. 6573-6584.
Shibuya, M., et al., "Differential Roles of Vascular Endothelial Growth Factor Receptor-1 and Receptor-2 in Angiogenesis", Journal of Biochemistry and Molecular Biology, 39(5): 469-478 (2006).

*Primary Examiner* — Ruixiang Li
(74) *Attorney, Agent, or Firm* — Proskauer Rose LLP; Fangli Chen; Julio J. Mendez

(57) ABSTRACT

The present invention provides, among other things, methods and compositions for treating muscular dystrophy, in particular, Duchenne muscular dystrophy (DMD). In some embodiments, a method according to the present invention includes administering to an individual who is suffering from or susceptible to DMD an effective amount of an anti-Flt-1 antibody, or antigen binding fragment thereof, such that at least one symptom or feature of DMD is reduced in intensity, severity, or frequency, or has delayed onset.

7 Claims, 14 Drawing Sheets

SEQUENCE LISTING

```
<160> NUMBER OF SEQ ID NOS: 3

<210> SEQ ID NO 1
<211> LENGTH: 21
<212> TYPE: PRT
<213> ORGANISM: Artificial Sequence
<220> FEATURE:
<223> OTHER INFORMATION: chemically synthesized peptide

<400> SEQUENCE: 1

Gly Ala Pro Gly Gly Gly Gly Ala Ala Ala Ala Ala Gly Gly Gly
1               5                   10                  15

Gly Gly Gly Ala Pro
            20
```

```
<210> SEQ ID NO 2
<211> LENGTH: 39
<212> TYPE: PRT
<213> ORGANISM: Artificial Sequence
<220> FEATURE:
<223> OTHER INFORMATION: chemically synthesized peptide

<400> SEQUENCE: 2

Gly Ala Pro Gly Gly Gly Gly Ala Ala Ala Ala Ala Gly Gly Gly
 1               5                  10                  15

Gly Gly Gly Ala Pro Gly Gly Gly Gly Ala Ala Ala Ala Ala Gly
            20                  25                  30

Gly Gly Gly Gly Gly Ala Pro
            35

<210> SEQ ID NO 3
<211> LENGTH: 57
<212> TYPE: PRT
<213> ORGANISM: Artificial Sequence
<220> FEATURE:
<223> OTHER INFORMATION: chemically synthesized peptide

<400> SEQUENCE: 3

Gly Ala Pro Gly Gly Gly Gly Ala Ala Ala Ala Ala Gly Gly Gly
 1               5                  10                  15

Gly Gly Gly Ala Pro Gly Gly Gly Gly Ala Ala Ala Ala Ala Gly
            20                  25                  30

Gly Gly Gly Gly Gly Ala Pro Gly Gly Gly Gly Ala Ala Ala Ala
            35                  40                  45

Ala Gly Gly Gly Gly Gly Ala Pro
    50                  55
```

ANTI-FLT-1 ANTIBODIES IN TREATING DUCHENNE MUSCULAR DYSTROPHY

CROSS-REFERENCE TO RELATED APPLICATIONS

The present application is a U.S. National Stage Application filed under 35 U.S.C. § 371 based on International Application No. PCT/US2014/013402, filed Jan. 28, 2014, which claims priority to U.S. Provisional Application Ser. No. 61/757,571 filed Jan. 28, 2013, the disclosure of each of which is incorporated herein by reference in their entirety.

BACKGROUND

Duchenne muscular dystrophy (DMD) is a recessive X-linked form of muscular dystrophy, affecting around 1 in 3,600 boys, which results in muscle degeneration and eventual death. The disorder is caused by a mutation in the dystrophin gene, located on the human X chromosome, which codes for the protein dystrophin, an important structural component within muscle tissue that provides structural stability to the dystroglycan complex (DGC) of the cell membrane. Dystrophin links the internal cytoplasmic actin filament network and extracellular matrix, providing physical strength to muscle fibers. Accordingly, alteration or absence of dystrophin results in abnormal sarcolemnal membrane function. While both sexes can carry the mutation, females rarely exhibit typical clinical features of the disease seen in boys.

Presently, there is no known cure for DMD. Several therapeutic avenues have been investigated including gene therapy and administration of corticosteroids. While some of these treatments may delay certain symptoms, there is presently no satisfactory therapeutic option for DMD patients.

SUMMARY OF THE INVENTION

The present invention provides, among other things, improved methods and compositions for treating muscular dystrophy, in particular, Duchenne muscular dystrophy (DMD) and/or Becker Muscular Dystrophy based on anti-Flt-1 antibody therapy. As described in the Examples below, the invention is, in part, based on the discovery that anti-Flt-1 antibodies, or antigen binding fragments thereof, can inhibit VEGF and other ligands from binding to the Flt-1 receptor, thereby increasing the amount VEGF and/or other ligands available to bind to VEGF receptors. Structural and functional improvements in DMD symptoms are improved. Indeed, as shown in the Examples, the present inventors have demonstrated that administration of an anti-Flt-1 antibody improves measures of muscle pathology as well as muscle function in an animal model of DMD. Therefore, the present invention provides safe and effective antibody-based therapeutics for the treatment of DMD.

In some embodiments, the present invention provides methods of treating Duchenne Muscular Dystrophy (DMD) comprising administering to an individual who is suffering from or susceptible to DMD an effective amount of an anti-Flt-1 antibody, or an antigen binding fragment thereof, such that at least one symptom or feature of DMD is reduced in intensity, severity, or frequency, or has delayed onset.

In some embodiments, an anti-Flt-1 antibody, or an antigen binding fragment thereof, is administered parenterally. In some embodiments, the parenteral administration is selected from intravenous, intradermal, intrathecal, inhalation, transdermal (topical), intraocular, intramuscular, subcutaneous, and/or transmucosal administration.

In some embodiments, an anti-Flt-1 antibody, or an antigen binding fragment thereof, is administered orally.

In some embodiments, an anti-Flt-1 antibody, or an antigen binding fragment thereof, is delivered to one or more target tissues selected from striated muscle (e.g., skeletal muscle, cardiac muscle). In some embodiments, the anti-Flt-1 antibody, or an antigen binding fragment thereof, is delivered to the heart. In some embodiments, the anti-Flt-1 antibody, or an antigen binding fragment thereof, is delivered to skeletal muscle. In some embodiments, the anti-Flt-1 antibody, or an antigen binding fragment thereof, is delivered to one or more skeletal muscles selected from Table 1. In some embodiments, the striated muscle (e.g., skeletal muscle) is selected from the group consisting of triceps, tibialis anterior, soleus, gastrocnemius, biceps, trapezius, deltoids, quadriceps, and diaphragm.

In some embodiments, the striated muscle is selected from the group consisting of triceps, tiablis anterior, soleus, gastrocnemius, biceps, trapezius, deltoids, quadriceps, and diaphragm.

In some embodiments an anti-Flt-1 antibody, or an antigen binding fragment thereof, is administered bimonthly, monthly, triweekly, biweekly, weekly, daily, or at variable intervals.

In some embodiments, the administration of an anti-Flt-1 antibody, or an antigen binding fragment thereof, results in muscle regeneration, fibrosis reduction, increased muscle strength, increased stability, increased flexibility, increased range of motion, increased stamina, reduced fatiguability, increased blood flow, improved cognition, improved pulmonary function, and/or inflammation inhibition.

In some embodiments, administration of an anti-Flt-1 antibody, or an antigen binding fragment thereof reduces the intensity, severity, or frequency, or delays the onset of at least one DMD symptom. In some embodiments administration of an anti-Flt-1 antibody, or an antigen binding fragment thereof reduces the intensity, severity, or frequency, or delays the onset of at least one DMD symptom selected from the group consisting of muscle wasting, muscle weakness, muscle fragility, muscle hypertrophy, muscle pseudohypertrophy, joint contracture, skeletal deformation, cardiomyopathy, impaired swallowing, impaired bowel and bladder function, muscle ischemia, cognitive impairment, behavioral dysfunction, socialization impairment, scoliosis, and impaired respiratory function.

In some embodiments, the present invention provides antibodies, or antigen binding fragments thereof that are characterized by an ability to inhibit VEGF binding to the Flt-1 receptor.

In some embodiments, an anti-Flt-1 antibody, or an antigen binding fragment thereof, is characterized with an ability to bind human Flt-1 with an affinity greater than $10^{-9}$ M, greater than $10^{-10}$ M, greater than $0.5 \times 10^{-10}$ M, greater than $10^{-11}$ M, greater than $0.5 \times 10^{-11}$ M, greater than $10^{-12}$ M, or greater than $0.5 \times 10^{-12}$ M, in a surface plasmon resonance (e.g., BIACORE) binding assay.

In some embodiments, an anti-Flt-1 antibody, or an antigen binding fragment thereof, is characterized with an $IC_{50}$ below 100 pM, below 10 pM, or below 1 pM in a competition assay with human Flt-1. In some embodiments, an anti-Flt-1 antibody, or antigen binding fragment thereof, is characterized with an $IC_{50}$ below 100 pM, below 10 pM, or below 1 pM for inhibition of binding of VEGF to human Flt-1 in a competition assay. In some embodiments, an anti-Flt-1 antibody, or antigen binding fragment thereof, is characterized with an $IC_{50}$ below 100 pM, below 10 pM, or below 1 pM for inhibition of binding of PLGF to human Flt-1 in a competition assay.

In some embodiments, an anti-Flt-1 antibody, or an antigen binding fragment thereof, does not bind to VEGFR2 (Flk-1) and/or VEGFR3 (Flt-4).

In some embodiments, an anti-Flt-1 antibody, or an antigen binding fragment thereof, binds to a mouse or monkey Flt-1. In some embodiments, an anti-Flt-1 antibody, or an antigen binding fragment thereof, does not bind to a mouse or monkey Flt-1.

In some embodiments, an anti-Flt-1 antibody, or an antigen binding fragment thereof, is selected from the group consisting of IgG, F(ab')$_2$, F(ab)$_2$, Fab', Fab, ScFvs, diabodies, triabodies and tetrabodies.

In some embodiments an anti-Flt-1 antibody, or an antigen binding fragment thereof, is IgG. In some embodiments an anti-Flt-1 antibody, or an antigen binding fragment thereof, is IgG1.

In some embodiments the anti-Flt-1 antibody, or an antigen binding fragment thereof, is a monoclonal antibody, and in certain embodiments is a humanized monoclonal antibody. In some embodiments, the humanized monoclonal antibody contains a human Fc region. In some embodiments, the Fc region contains one or more mutations that enhance the binding affinity between the Fc region and the FcRn receptor such that the in vivo half-life of the antibody is prolonged. In some embodiments, the Fc region contains one or more mutations at one or more positions corresponding to Thr 250, Met 252, Ser 254, Thr 256, Thr 307, Glu 380, Met 428, His 433 and/or Asn 434 of human IgG1.

In some embodiments, the present invention provides a pharmaceutical composition comprising an anti-Flt-1 antibody, or an antigen binding fragment thereof, and a pharmaceutically acceptable carrier.

As used in this application, the terms "about" and "approximately" are used as equivalents. Any numerals used in this application with or without about/approximately are meant to cover any normal fluctuations appreciated by one of ordinary skill in the relevant art.

Other features, objects, and advantages of the present invention are apparent in the detailed description that follows. It should be understood, however, that the detailed description, while indicating embodiments of the present invention, is given by way of illustration only, not limitation. Various changes and modifications within the scope of the invention will become apparent to those skilled in the art from the detailed description.

DEFINITIONS

Figure 1:
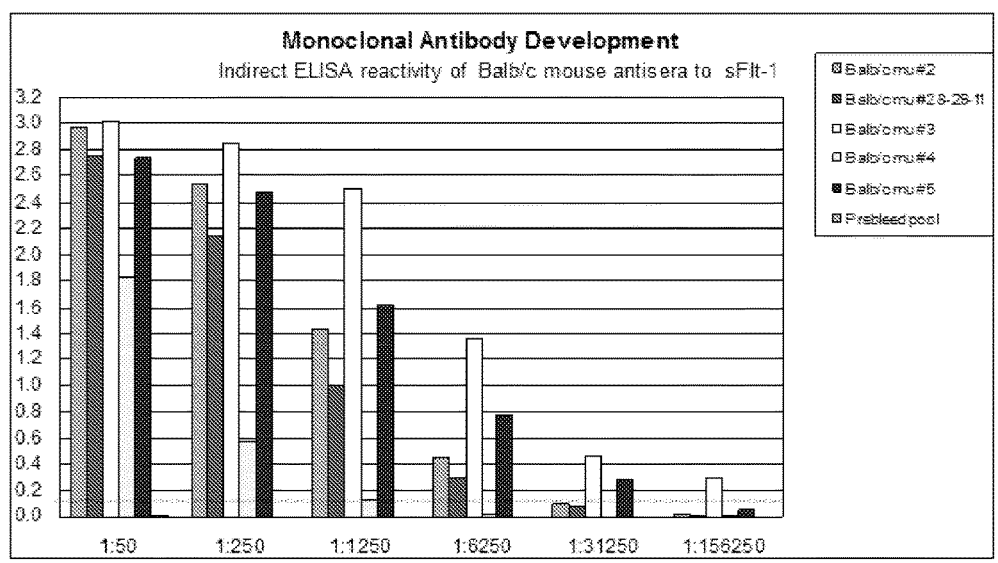
FIG. 1 shows exemplary results illustrating the anti-soluble human Flt-1 antiserum titer of mice immunized with soluble human Flt-1 antigen. Anti-sFlt-1 serum titer is depicted from five separate Balb/c mice 20 days following administration.

In order for the present invention to be more readily understood, certain terms are first defined below. Additional definitions for the following terms and other terms are set forth throughout the specification.

Animal: As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate and/or a pig). In some embodiments, animals include, but are not limited to, mammals, birds, reptiles, amphibians, fish, insects, and/or worms. In some embodiments, an animal may be a transgenic animal, genetically-engineered animal, and/or a clone.

Antibody: As used herein, the term "antibody" refers to any immunoglobulin, whether natural or wholly or partially synthetically produced. All derivatives thereof which maintain specific binding ability are also included in the term. The term also covers any protein having a binding domain which is homologous or largely homologous to an immunoglobulin-binding domain. Such proteins may be derived from natural sources, or partly or wholly synthetically produced. An antibody may be monoclonal or polyclonal. An antibody may be a member of any immunoglobulin class, including any of the human classes: IgG, IgM, IgA, IgD, and IgE. In certain embodiments, an antibody may be a member of the IgG immunoglobulin class. As used herein, the terms "antibody fragment" or "characteristic portion of an antibody" are used interchangeably and refer to any derivative of an antibody which is less than full-length. In general, an antibody fragment retains at least a significant portion of the full-length antibody's specific binding ability. Examples of antibody fragments include, but are not limited to, Fab, Fab', F(ab')$_2$, scFv, Fv, dsFv diabody, and Fd fragments. An antibody fragment may be produced by any means. For example, an antibody fragment may be enzymatically or chemically produced by fragmentation of an intact antibody and/or it may be recombinantly produced from a gene encoding the partial antibody sequence. Alternatively or additionally, an antibody fragment may be wholly or partially synthetically produced. An antibody fragment may optionally comprise a single chain antibody fragment. Alternatively or additionally, an antibody fragment may comprise multiple chains which are linked together, for example, by disulfide linkages. An antibody fragment may optionally comprise a multimolecular complex. A functional antibody fragment typically comprises at least about 50 amino acids and more typically comprises at least about 200 amino acids. In some embodiments, an antibody may be a human antibody. In some embodiments, an antibody may be a humanized antibody.

Antigen binding fragment: As used herein, the term "antigen binding fragment" refers to a portion of an immunoglobulin molecule that contacts and binds to an antigen (i.e., Flt-1).

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Biologically active: As used herein, the phrase "biologically active" refers to a characteristic of any agent that has activity in a biological system, and particularly in an organism. For instance, an agent that, when administered to an organism, has a biological effect on that organism, is considered to be biologically active. In particular embodiments, where a peptide is biologically active, a portion of that peptide that shares at least one biological activity of the peptide is typically referred to as a "biologically active" portion. In certain embodiments, a peptide has no intrinsic biological activity but that inhibits the binding of one or more VEGF ligands, is considered to be biologically active.

Carrier or diluent: As used herein, the terms "carrier" and "diluent" refer to a pharmaceutically acceptable (e.g., safe and non-toxic for administration to a human) carrier or diluting substance useful for the preparation of a pharmaceutical formulation. Exemplary diluents include sterile water, bacteriostatic water for injection (BWFI), a pH buffered solution (e.g. phosphate-buffered saline), sterile saline solution, Ringer's solution or dextrose solution.

Dosage form: As used herein, the terms "dosage form" and "unit dosage form" refer to a physically discrete unit of a therapeutic protein (e.g., antibody) for the patient to be treated. Each unit contains a predetermined quantity of active material calculated to produce the desired therapeutic effect. It will be understood, however, that the total dosage of the composition will be decided by the attending physician within the scope of sound medical judgment.

Functional Equivalent or derivative: As used herein, the term "functional equivalent" or "functional derivative" denotes, in the context of a functional derivative of an amino acid sequence, a molecule that retains a biological activity (either function or structural) that is substantially similar to that of the original sequence. A functional derivative or equivalent may be a natural derivative or is prepared synthetically. Exemplary functional derivatives include amino acid sequences having substitutions, deletions, or additions of one or more amino acids, provided that the biological activity of the protein is conserved. The substituting amino acid desirably has chemico-physical properties which are similar to that of the substituted amino acid. Desirable similar chemico-physical properties include similarities in charge, bulkiness, hydrophobicity, hydrophilicity, and the like.

Fusion Protein: As used herein, the term "fusion protein" or "chimeric protein" refers to a protein created through the joining of two or more originally separate proteins, or portions thereof. In some embodiments, a linker or spacer will be present between each protein.

Half-Life: As used herein, the term "half-life" is the time required for a quantity such as protein concentration or activity to fall to half of its value as measured at the beginning of a time period.

Hypertrophy: As used herein the term "hypertrophy" refers to the increase in volume of an organ or tissue due to the enlargement of its component cells.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control subject (or multiple control subject) in the absence of the treatment described herein. A "control subject" is a subject afflicted with the same form of disease as the subject being treated, who is about the same age as the subject being treated.

In Vitro: As used herein, the term "in vitro" refers to events that occur in an artificial environment, e.g., in a test tube or reaction vessel, in cell culture, etc., rather than within a multi-cellular organism.

In Vivo: As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

Linker: As used herein, the term "linker" refers to, in a fusion protein, an amino acid sequence other than that appearing at a particular position in the natural protein and is generally designed to be flexible or to interpose a structure, such as an α-helix, between two protein moieties. A linker is also referred to as a spacer. A linker or a spacer typically does not have biological function on its own.

Pharmaceutically acceptable: The term "pharmaceutically acceptable" as used herein, refers to substances that, within the scope of sound medical judgment, are suitable for use in contact with the tissues of human beings and animals without excessive toxicity, irritation, allergic response, or other problem or complication, commensurate with a reasonable benefit/risk ratio.

Polypeptide: The term "polypeptide" as used herein refers to a sequential chain of amino acids linked together via peptide bonds. The term is used to refer to an amino acid chain of any length, but one of ordinary skill in the art will understand that the term is not limited to lengthy chains and can refer to a minimal chain comprising two amino acids linked together via a peptide bond. As is known to those skilled in the art, polypeptides may be processed and/or modified.

Prevent: As used herein, the term "prevent" or "prevention", when used in connection with the occurrence of a disease, disorder, and/or condition, refers to reducing the risk of developing the disease, disorder and/or condition. See the definition of "risk."

Protein: The term "protein" as used herein refers to one or more polypeptides that function as a discrete unit. If a single polypeptide is the discrete functioning unit and does not require permanent or temporary physical association with other polypeptides in order to form the discrete functioning unit, the terms "polypeptide" and "protein" may be used interchangeably. If the discrete functional unit is comprised of more than one polypeptide that physically associate with one another, the term "protein" refers to the multiple polypeptides that are physically coupled and function together as the discrete unit.

Risk: As will be understood from context, a "risk" of a disease, disorder, and/or condition comprises a likelihood that a particular individual will develop a disease, disorder, and/or condition (e.g., DMD). In some embodiments, risk is expressed as a percentage. In some embodiments, risk is from 0, 1, 2, 3, 4, 5, 6, 7, 8, 9, 10, 20, 30, 40, 50, 60, 70, 80, 90 up to 100%. In some embodiments risk is expressed as a risk relative to a risk associated with a reference sample or group of reference samples. In some embodiments, a reference sample or group of reference samples have a known risk of a disease, disorder, condition and/or event (e.g., DMD). In some embodiments a reference sample or group of reference samples are from individuals comparable to a particular individual. In some embodiments, relative risk is 0, 1, 2, 3, 4, 5, 6, 7, 8, 9, 10, or more.

Striated muscle: As used herein, the term "striated muscle" refers to multinucleated muscle tissue with regular arrangement of their intracellular contractile units, sarcomeres, leading to the appearance of striations using microscopy and under voluntary control. Typically, striated muscle can be cardiac muscle, skeletal muscle, and Branchiomeric muscles.

Smooth muscle: As used herein, the term "smooth muscle" refers to involuntarily controlled, non-striated muscle, including unitary and multi-unit muscle.

Subject: As used herein, the term "subject" refers to a human or any non-human animal (e.g., mouse, rat, rabbit, dog, cat, cattle, swine, sheep, horse or primate). A human includes pre- and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or susceptible to a disease or disorder but may or may not display symptoms of the disease or disorder.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Substantial homology: The phrase "substantial homology" is used herein to refer to a comparison between amino acid or nucleic acid sequences. As will be appreciated by those of ordinary skill in the art, two sequences are generally considered to be "substantially homologous" if they contain homologous residues in corresponding positions. Homologous residues may be identical residues. Alternatively, homologous residues may be non-identical residues will appropriately similar structural and/or functional characteristics. For example, as is well known by those of ordinary skill in the art, certain amino acids are typically classified as "hydrophobic" or "hydrophilic" amino acids, and/or as having "polar" or "non-polar" side chains. Substitution of one amino acid for another of the same type may often be considered a "homologous" substitution.

As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., basic local alignment search tool, *J. Mol. Biol.*, 215(3): 403-410, 1990; Altschul, et al., *Methods in Enzymology*; Altschul, et al., "Gapped BLAST and PSI-BLAST: a new generation of protein database search programs", *Nucleic Acids Res.* 25:3389-3402, 1997; Baxevanis, et al., *Bioinformatics: A Practical Guide to the Analysis of Genes and Proteins*, Wiley, 1998; and Misener, et al., (eds.), *Bioinformatics Methods and Protocols* (Methods in Molecular Biology, Vol. 132), Humana Press, 1999. In addition to identifying homologous sequences, the programs mentioned above typically provide an indication of the degree of homology. In some embodiments, two sequences are considered to be substantially homologous if at least 50%, 55%, 60%, 65%, 70%, 75%, 80%, 85%, 90%, 91%, 92%, 93%, 94%, 95%, 96%, 97%, 98%, 99% or more of their corresponding residues are homologous over a relevant stretch of residues. In some embodiments, the relevant stretch is a complete sequence. In some embodiments, the relevant stretch is at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more residues.

Substantial identity: The phrase "substantial identity" is used herein to refer to a comparison between amino acid or nucleic acid sequences. As will be appreciated by those of ordinary skill in the art, two sequences are generally considered to be "substantially identical" if they contain identical residues in corresponding positions. As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, *J. Mol. Biol.*, 215(3): 403-410, 1990; Altschul, et al., *Methods in Enzymology*; Altschul et al., *Nucleic Acids Res.* 25:3389-3402, 1997; Baxevanis et al., *Bioinformatics: A Practical Guide to the Analysis of Genes and Proteins*, Wiley, 1998; and Misener, et al., (eds.), *Bioinformatics Methods and Protocols* (Methods in Molecular Biology, Vol. 132), Humana Press, 1999. In addition to identifying identical sequences, the programs mentioned above typically provide an indication of the degree of identity. In some embodiments, two sequences are considered to be substantially identical if at least 50%, 55%, 60%, 65%, 70%, 75%, 80%, 85%, 90%, 91%, 92%, 93%, 94%, 95%, 96%, 97%, 98%, 99% or more of their corresponding residues are identical over a relevant stretch of residues. In some embodiments, the relevant stretch is a complete sequence. In some embodiments, the relevant stretch is at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more residues.

Suffering from: An individual who is "suffering from" a disease, disorder, and/or condition has been diagnosed with or displays one or more symptoms of the disease, disorder, and/or condition.

Susceptible to: An individual who is "susceptible to" a disease, disorder, and/or condition has not been diagnosed with the disease, disorder, and/or condition. In some embodiments, an individual who is susceptible to a disease, disorder, and/or condition may not exhibit symptoms of the disease, disorder, and/or condition. In some embodiments, an individual who is susceptible to a disease, disorder, condition, or event (for example, DMD) may be characterized by one or more of the following: (1) a genetic mutation associated with development of the disease, disorder, and/or condition; (2) a genetic polymorphism associated with development of the disease, disorder, and/or condition; (3) increased and/or decreased expression and/or activity of a protein associated with the disease, disorder, and/or condition; (4) habits and/or lifestyles associated with development of the disease, disorder, condition, and/or event (5) having undergone, planning to undergo, or requiring a transplant. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Target tissues: As used herein, the term "target tissues" refers to any tissue that is affected by a disease to be treated such as DMD. In some embodiments, target tissues include those tissues that display disease-associated pathology, symptom, or feature, including but not limited to muscle wasting, skeletal deformation, cardiomyopathy, muscle ischemia, cognitive impairment, and impaired respiratory function Therapeutically effective amount: As used herein, the term "therapeutically effective amount" of a therapeutic agent means an amount that is sufficient, when administered to a subject suffering from or susceptible to a disease, disorder, and/or condition, to treat, diagnose, prevent, and/or delay the onset of the symptom(s) of the disease, disorder, and/or condition. It will be appreciated by those of ordinary skill in the art that a therapeutically effective amount is typically administered via a dosing regimen comprising at least one unit dose.

Treating: As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a particular disease, disorder, and/or condition. Treatment may be administered to a subject who does not exhibit signs of a disease and/or exhibits only early signs of the disease for the purpose of decreasing the risk of developing pathology associated with the disease.

DETAILED DESCRIPTION OF CERTAIN EMBODIMENTS

The present invention provides, among other things, methods and compositions for treating muscular dystrophy, including Duchenne muscular dystrophy (DMD) and/or Becker Muscular Dystrophy, based on anti-Flt-1 antibodies, or antigen binding fragments thereof, as therapeutics. In some embodiments, the present invention provides methods of treating DMD including administering to an individual who is suffering from or susceptible to DMD an effective amount of an Flt-1 antibody or antigen binding fragment thereof such that at least one symptom or feature of DMD is reduced in intensity, severity, or frequency, or has delayed onset.

Various aspects of the invention are described in detail in the following sections. The use of sections is not meant to limit the invention. Each section can apply to any aspect of the invention. In this application, the use of "or" means "and/or" unless stated otherwise.

Duchenne Muscular Dystrophy (DMD)

DMD is a disease characterized by progressive deterioration of muscles and loss of muscle related functions throughout the body. It is contemplated that the present invention provides methods and compositions for slowing, delaying or preventing deterioration of muscles, regenerating muscle and reversing, eliminating, delaying, preventing, or minimizing fibrosis, inflammation and other symptoms or features associated with DMD and other muscular dystrophies in various muscle tissues.

Muscle Tissues

There are two major types of muscle tissue in an animal—striated muscle and smooth muscle. As used herein, the term "striated muscle" refers to muscle tissues containing repeating sarcomeres. Striated muscle tends to be under voluntary control and attached to the skeleton. Striated muscle allows for voluntary movement of the body and includes the major muscle groups including the quadriceps, gastrocnemius, biceps, triceps, trapezius, deltoids, and many others. Striated muscle tends to be very long and, many striated muscles are able to function independently. Some striated muscle, however, is not attached to the skeleton, including those in the mouth, anus, heart, and upper portion of the esophagus.

Smooth muscle, on the other hand, has very different structure. Rather than a series of long muscles with separate skeletal attachments, smooth muscle tends to be organized into continuous sheets with mechanical linkages between smooth muscle cells. Smooth muscle is often located in the walls of hollow organs and is usually not under voluntary control. Smooth muscles lining a particular organ must bear the same load and contract concurrently. Smooth muscle functions, at least in part, to handle changes in load on hollow organs caused by movement and/or changes in posture or pressure. This dual role means that smooth muscle must not only be able to contract like striated muscle, but also that it must be able to contract tonically to maintain organ dimensions against sustained loads. Examples of smooth muscles are those lining blood vessels, bronchioles, bladder, and gastrointestinal tract such as rectum.

The strength of a muscle depends on the number and sizes of the muscle's cells and on their anatomic arrangement. Increasing the diameter of a muscle fiber either by synthesis of new myofibrils (hypertrophy) and/or the formation of more muscle cells (hyperplasia) will increase the force-generating capacity of the muscle.

Muscles may also be grouped by location or function. In some embodiments, an Flt-1 antibody or antigen binding fragment thereof is targeted to one or more muscles of the face, one or more muscles for mastication, one or more muscles of the tongue and neck, one or more muscles of the thorax, one or more muscles of the pectoral girdle and arms, one or more muscles of the arm and shoulder, one or more ventral and dorsal forearm muscles, one or more muscles of the hand, one or more muscles of the erector spinae, one or more muscles of the pelvic girdle and legs, and/or one or more muscles of the foreleg and foot.

In some embodiments, muscles of the face include, but are not limited to, intraocular muscles such as ciliary, iris dilator, iris sphincter; muscles of the ear such as auriculares, temporoparietalis, stapedius, tensor tympani; muscles of the nose such as procerus, nasalis, dilator naris, depressor septi nasi, levator labii superioris alaeque nasi; muscles of the mouth such as levator anguli oris, depressor anguli oris, orbicularis oris, Buccinator, Zygomaticus Major and Minor, Platysma, Levator Labii Superioris, Depressor Labii Inferioris, Risorius, Mentalis, and/or Corrugator Supercilii.

In some embodiments, muscles of mastication include, but are not limited to, Masseter, Temporalis, Medial Pterygoid, Lateral Pterygoid. In some embodiments, muscles of the tongue and neck include, but are not limited to, Genioglossus, Styloglossus, Palatoglossus, Hyoglossus, Digastric, Stylohyoid, Mylohyoid, Geniohyoid, Omohyoid, Sternohyoid, Sternothyroid, Thyrohyoid, Sternocleidomastoid, Anterior Scalene, Middle Scalene, and/or Posterior Scalene.

In some embodiments, muscles of the thorax, pectoral girdle, and arms include, but are not limited to, Subclavius Pectoralis major, Pectoralis minor, Rectus abdominis, External abdominal oblique, Internal abdominal oblique, Transversus Abdominis, Diaphragm, External Intercostals, Internal Intercostals, Serratus Anterior, Trapezius, Levator Scapulae, Rhomboideus Major, Rhomboideus Minor, Latissimus dorsi, Deltoid, subscapularis, supraspinatus, infraspinatus, Teres major, Teres minor, and/or Coracobrachialis.

In some embodiments, muscles of the arm and shoulder include, but are not limited to, Biceps brachii-Long Head, Biceps brachii-Short Head, Triceps brachii-Long Head, Triceps brachii Lateral Head, Triceps brachii-Medial Head, Anconeus, Pronator teres, Supinator, and/or Brachialis.

In some embodiments, muscles of the ventral and dorsal forearm include, but are not limited to, Brachioradialis, Flexor carpi radialis, Flexor carpi ulnaris, Palmaris longus, Extensor carpi ulnaris, Extensor carpi radialis longus, Extensor carpi radialis brevis, Extensor digitorum, Extensor digiti minimi.

In some embodiments, muscles of the hand include, but are not limited to intrinsic muscles of the hand such as thenar, abductor pollicis brevis, flexor pollicis brevis, opponens pollicis, hypothenar, abductor digiti minimi, the flexor digiti minimi brevis, opponens digiti minimi, palmar interossei, dorsal interossei and/or lumbricals.

In some embodiments, muscles of the erector spinae include, but are not limited to, cervicalis, spinalis, longissimus, and/or iliocostalis.

In some embodiments, muscles of the pelvic girdle and the legs include, but are not limited to, Psoas Major, Iliacus, quadratus femoris, Adductor longus, Adductor brevis, Adductor magnus, Gracilis, Sartorius, Quadriceps femoris such as, rectus femoris, vastus lateralis, vastus medialis, vastus intermedius, Gastrocnemius, Fibularis (Peroneus) Longus, Soleus, Gluteus maximus, Gluteus medius, Gluteus minimus, Hamstrings: Biceps Femoris: Long Head, Hamstrings: Biceps Femoris: Short Head, Hamstrings: Semitendinosus, Hamstrings: Semimembranosus, Tensor fasciae latae, Pectineus, and/or Tibialis anterior.

In some embodiments, muscles of the foreleg and foot include, but are not limited to, Extensor digitorum longus, Extensor hallucis longus, peroneus brevis, plantaris, Tibialis posterior, Flexor hallucis longus, extensor digitorum brevis, extensor hallucis brevis, Abductor hallucis, flexor hallucis brevis, Abductor digiti minimi, flexor digiti minimi, opponens digiti minimi, extensor digitorum brevis, lumbricales of the foot, Quadratus plantae or flexor accessorius, flexor digitorum brevis, dorsal interossei, and/or plantar interossei.

Exemplary muscle targets are summarized in Table 1.

TABLE 1

| ORBICULARIS OCULI | | | |
|---|---|---|---|
| Intraocular: ciliary, iris dilator, iris sphincter | | | |
| Ear: auriculares, temporoparietalis, stapedius, tensor tympani | | | |
| Nose: procerus, nasalis, dilator naris, depressor septi nasi, levator labii superioris alaeque nasi | | | |
| Mouth: levator anguli oris, depressor anguli oris, orbicularis oris | | | |
| Buccinator | Zygomaticus Major and Minor | Platysma | Levator Labii Superioris |
| Depressor Labii Inferioris | Risorius | Mentalis | Corrugator Supercilii |
| Anconeus | Pronator teres | Supinator | Brachialis |
| MUSCLES OF MASTICATON | | | |
| Masseter | Temporalis | Medial Pterygoid | Lateral Pterygoid |
| MUSCLES OF THE TONGUE AND NECK | | | |
| Genioglossus | Styloglossus | Palatoglossus | Hyoglossus |
| Digastric | Stylohyoid | Mylohyoid | Geniohyoid |
| Omohyoid | Sternohyoid | Sternothyroid | Thyrohyoid |
| Sternocleidomastoid | Anterior Scalene | Middle Scalene | Posterior Scalene |
| MUSCLES OF THE THORAX, PECTORAL GIRDLE AND ARMS | | | |
| Subclavius | Pectoralis major | Pectoralis minor | Rectus abdominis |
| External abdominal oblique | Internal abdominal oblique | Transversus Abdominis | Diaphragm |
| External Intercostals | Internal Intercostals | Serratus Anterior | Trapezius |
| Levator Scapulae | Rhomboideus Major | Rhomboideus Minor | Latissimus dorsi |
| Deltoid | subscapularis | supraspinatus | infraspinatus |
| Teres major | Teres minor | Coracobrachialis | |
| ARM AND SHOULDER | | | |
| Biceps brachii-Long Head | Biceps brachii-Short Head | Triceps brachii-Long Head | Triceps brachii-Lateral Head |
| Triceps brachii-Medial Head | Anconeus | Pronator teres | Supinator |
| Brachialis | | | |
| FOREARM MUSCLES: Ventral and Dorsal | | | |
| Brachioradialis | Flexor carpi radialis | Flexor carpi ulnaris | Palmaris longus |
| Extensor carpi ulnaris | Extensor carpi radialis longus | Extensor carpi radialis brevis | Extensor digitorum |
| Extensor digiti minimi | erector spinae: cervicalis | erector spinae: spinalis | erector spinae: longissimus |
| erector spinae: iliocostalis | | | |
| Intrinsic Muscles of the Hand: thenar, abductor pollicis brevis, flexor pollicis brevis, and the opponens pollicis | | | |
| Intrinsic Muscles of the Hand: hypothenar, abductor digiti minimi, the flexor digiti minimi brevis, and the opponens digiti minimi | | | |
| Intrinsic Muscles of the Hand: palmar interossei, dorsal interossei and lumbricals | | | |
| MUSCLES OF THE PELVIC GIRDLE AND THE LEGS | | | |
| Iliopsoas: Psoas Major | Iliopsoas: Iliacus | quadratus femoris | Adductor longus |
| Adductor brevis | Adductor magnus | Gracilis | Sartorius |
| Quadriceps femoris: rectus femoris | Quadriceps femoris: vastus lateralis | Quadriceps femoris: vastus medialis | Quadriceps femoris: vastus intermedius |
| Gastrocnemius | Fibularis (Peroneus) Longus | Soleus | Gluteus maximus |

TABLE 1-continued

| | | | |
|---|---|---|---|
| Gluteus medius | Gluteus minimus | Hamstrings: Biceps Femoris: Long Head | Hamstrings: Biceps Femoris: Short Head |
| Hamstrings: Semitendinosus | Hamstrings: Semimembranosus | Tensor fasciae latae | Pectineus |
| Tibialis anterior | | | |
| MUSCLES OF THE FORELEG AND FOOT | | | |
| Extensor digitorum longus | Extensor hallucis longus | peroneus brevis | plantaris |
| Tibialis posterior | Flexor hallucis longus | extensor digitorum brevis | extensor hallucis brevis |
| Abductor hallucis | flexor hallucis brevis | Abductor digiti minimi | flexor digiti minimi |
| opponens digiti minimi | extensor digitorum brevis | lumbricales of the foot | Quadratus plantae or flexor accessorius |
| Flexor digitorum brevis | dorsal interossei | plantar interossei | |

Muscular Dystrophy

Muscular dystrophies are a group of inherited disorders that cause degeneration of muscle, leading to weak and impaired movements. A central feature of all muscular dystrophies is that they are progressive in nature. Muscular dystrophies include, but are not limited to: Duchenne muscular dystrophy (DMD), Becker muscular dystrophy, Emery-Dreifuss muscular dystrophy, facioscapulohumeral muscular dystrophy, limb-girdle muscular dystrophies, and myotonic dystrophy Types 1 and 2, including the congenital form of Myotonic dystrophy Type 1. Symptoms may vary by type of muscular dystrophy with some or all muscles being affected. Exemplary symptoms of muscular dystrophies include delayed development of muscle motor skills, difficulty using one or more muscle groups, difficulty swallowing, speaking or eating, drooling, eyelid drooping, frequent falling, loss of strength in a muscle or group of muscles as an adult, loss in muscle size, problems walking due to weakness or altered biomechanics of the body, and/or cognitive or behavioral impairment/mental retardation.

While there are no known cures for muscular dystrophies, several supportive treatments are used which include both symptomatic and disease modifying therapies. Corticosteroids, ACE inhibitors, Angiotensin receptor Blockers, physical therapy, orthotic devices, wheelchairs, or other assistive medical devices for ADLs and pulmonary function are commonly used in muscular dystrophies. Cardiac pacemakers are used to prevent sudden death from cardiac arrythmias in Myotonic dystrophy. Anti-myotonic agents which improve the symptoms of myotonia (inability to relax) include mexilitine, and in some cases phenytoin, procainamide and quinine.

Duchenne Muscular Dystrophy

Duchenne muscular dystrophy (DMD) is a recessive X-linked form of muscular dystrophy which results in muscle degeneration and eventual death. DMD is characterized by weakness in the proximal muscles, abnormal gait, hypertrophy in the gastrocnemius (calf) muscles, and elevated creatine kinase. Many DMD patients are diagnosed around the age of 5, when symptoms/signs typically become more obvious. Affected individuals typically stop walking around age 10-13 and die in or before their mid to late 20's due to cardiorespiratory dysfunction.

The disorder DMD is caused by a mutation in the dystrophin gene, located on the human X chromosome, which codes for the protein dystrophin, an important structural component within muscle tissue that provides structural stability to the dystroglycan complex (DGC) of the cell membrane. Dystrophin links the internal cytoplasmic actin filament network and extracellular matrix, providing physical strength to muscle fibers. Accordingly, alteration or absence of dystrophin results in abnormal sarcolemnal membrane tearing and necrosis of muscle fibers. While both sexes can carry the mutation, females rarely exhibit severe signs of the disease.

A main symptom of DMD is muscle weakness associated with muscle wasting with the voluntary muscles being first affected typically, especially affecting the muscles of the hips, pelvic area, thighs, shoulders, and calf muscles. Muscle weakness also occurs in the arms, neck, and other areas. Calves are often enlarged. Signs and symptoms usually appear before age 6 and may appear as early as infancy. Other physical symptoms include, but are not limited to, delayed ability to walk independently, progressive difficulty in walking, stepping, or running, and eventual loss of ability to walk (usually by the age of 12); frequent falls; fatigue; difficulty with motor skills (running, hopping, jumping); increased lumbar lordosis, leading to shortening of the hip-flexor muscles; impaired functionality of achilles tendon and hamstrings, fibrosis in connective tissue; muscle fiber deformities; pseudohypertrophy (enlarging) of tongue and calf muscles caused by replacement of muscle tissue by fat and connective tissue; higher risk of neurobehavioral disorders (e.g., ADHD), learning disorders (dyslexia), and non-progressive weaknesses in specific cognitive skills (in particular short-term verbal memory); skeletal deformities (including scoliosis in some cases).

Flt-1 Receptor

Flt-1 receptor, also known as vascular endothelial growth factor receptor 1, is a receptor that is encoded by the FLT1 gene. The vascular endothelial growth factor (VEGF) family of signal glycoproteins act as potent promoters of angiogenesis during embryogenesis and postnatal growth. Specifically, the binding of the VEGF-A ligand with the VEGF receptors has been shown to promote vascular permeability and also trigger endothelial cell migration, proliferation, and survival, and the newly formed endothelial cells provide the basic structure of new vasculatures. The dominant VEGF signal molecule for angiogenesis, VEGF-A, mediates its signal through VEGF receptor-1 (VEGFR-1, also known as Flt-1) and VEGF receptor-2 (VEGFR-2, also known as Flk-1). A soluble form of Flt-1 (sFlt-1) also exists, but lacks an intracellular signaling domain and thus is believed to only serve in a regulatory capacity by sequestering VEGF-A or other ligands that bind to it. sFlt-1 and other molecules containing Flt-1 binding sites that are not linked to an intracellular signal transduction pathway are referred to as "decoy receptors". Flt-1 and Flk-1 receptors contain an extracellular VEGF-A-binding domain and an intracellular tyrosine kinase domain, and both show expression during the developmental stage and tissue regeneration in hemangioblasts and endothelial cell lineages. Flt-1 has about 10 times greater binding affinity for VEGF-A (Kd ~2-10 pM) compared to Flk-1, but the weaker tyrosine kinase domain indicates that angiogenic signal transduction following VEGF-A binding to Flt-1 is comparably weaker than the Flk-1 signal. As such, homozygous Flt-1 gene knockout mice die in the embryonic stage from endothelial cell overproduction and blood vessel disorganization. Inversely, homozygous Flk-1 gene knockout mice die from defects in the development of organized blood vessels due to lack of yolk-sac blood island formation during embryogenesis. Both the Flt-1 and Flk-1 receptors are needed for normal development, but selective augmentation in VEGF-A concentration may allow for greater binding to the Flk-1 receptor and induce a pro-angiogenic effect that increases capillary density and facilitates regeneration of muscle, reduction of fibrosis and inflammation, and mitigation of symptoms and features associated with DMD and other muscular dystrophies in various muscle tissues.

As used herein, the term "Flt-1 receptor" refers to both soluble and membrane associate Flt-1 receptors, or functional fragments thereof.

Anti-Flt-1 Antibodies

As used herein, the term "anti-Flt-1 antibodies" refers to any antibodies, or antigen binding fragments thereof, that bind to an Flt-1 receptor (e.g., soluble or membrane associated Flt-1 receptor). In some embodiments, anti-Flt-1 antibodies are produced that bind with high affinity to Flt-1 receptors. Without wishing to be bound by theory, it is believed that anti-Flt-1 antibody binding to Flt-1 receptors inhibits one or more endogenous ligands from binding to Flt-1 and thereby allowing a greater amount of available ligand to associate with other VEGF receptors, such as the Flk-1 receptor. In some embodiments, antibody binding to Flt-1 receptors increases the amount of VEGF available to bind to other VEGF receptors. In some embodiments, antibody binding to Flt-1 receptors increases the amount of placental growth factor (PLGF) available to bind to other VEGF receptors.

In some embodiments, an anti-Flt-1 antibody, or an antigen binding fragment thereof, binds human Flt-1 with an affinity greater than about $10^{-9}$ M, greater than about $10^{-10}$ M, greater than about $0.5 \times 10^{-10}$ M, greater than about $10^{-11}$ M, greater than about $0.5 \times 10^{-11}$ M, greater than about $10^{-12}$ M, or greater than about $0.5 \times 10^{-12}$ M. The affinity of an Flt-1 antibody may be measured, for example, in a surface plasmon resonance assay, such as a BIACORE assay.

In some embodiments, an anti-Flt-1 antibody, or an antigen binding fragment thereof, is characterized by an $IC_{50}$ below 100 pM, below 10 pM, or below 1 pM in a competition assay with human Flt-1.

In some embodiments, an anti-Flt-1 antibody, or an antigen binding fragment thereof inhibits the binding and/or activity of VEGF at the Flt-1 receptor. In some embodiments, an anti-Flt-1 antibody, or an antigen binding fragment thereof, is characterized by an $IC_{50}$ below 100 pM, below 10 pM, or below 1 pM for inhibition of binding of VEGF to human Flt-1 in a competition assay.

In some embodiments, an anti-Flt-1 antibody, or an antigen binding fragment thereof inhibits the binding and/or activity of PLGF at the Flt-1 receptor. In some embodiments, an anti-Flt-1 antibody, or an antigen binding fragment thereof, is characterized by an $IC_{50}$ below 100 pM, below 10 pM, or below 1 pM for inhibition of binding of PLGF to human Flt-1 in a competition assay.

In some embodiments, an anti-Flt-1 antibody, or an antigen binding fragment thereof selectively binds Flt-1 and has minimal or no appreciable binding to other VEGF receptors. In some embodiments, an anti-Flt-1 antibody, or an antigen binding fragment thereof selectively binds Flt-1 and has minimal or no appreciable binding to VEGFR2 (Flk-1) and/or VEGFR3 (Flt-4).

In some embodiments, an anti-Flt-1 antibody, or an antigen binding fragment thereof selectively binds human Flt-1, and has minimal or no appreciable binding to other mammalian Flt-1 receptors (e.g., with a binding affinity less than $10^{-7}$M or $10^{-6}$M). In some embodiments, an anti-Flt-1 antibody, or an antigen binding fragment thereof selectively binds human Flt-1 and does not bind to monkey Flt-1. In some embodiments, an anti-Flt-1 antibody, or an antigen binding fragment thereof selectively binds human Flt-1 and does not bind to mouse Flt-1.

In some embodiments, an anti-Flt-1 antibody, or an antigen binding fragment thereof binds human Flt-1 as well as monkey Flt-1. In some embodiments an anti-Flt-1 antibody, or an antigen binding fragment thereof binds human Flt-1 as well as mouse Flt-1.

In some embodiments, an anti-Flt-1 antibody, or an antigen binding fragment thereof, is selected from the group consisting of IgG, F(ab')$_2$, F(ab)$_2$, Fab', Fab, ScFvs, diabodies, triabodies and tetrabodies.

In some embodiments an anti-Flt-1 antibody, or an antigen binding fragment thereof, is IgG. In some embodiments an anti-Flt-1 antibody, or an antigen binding fragment thereof, is IgG1.

In some embodiments, a suitable anti-Flt-1 antibody contains an Fc domain or a portion thereof that binds to the FcRn receptor. As a non-limiting example, a suitable Fc domain may be derived from an immunoglobulin subclass such as IgG. In some embodiments, a suitable Fc domain is derived from IgG1, IgG2, IgG3, or IgG4. Particularly suitable Fc domains include those derived from human or humanized antibodies.

It is contemplated that improved binding between Fc domain and the FcRn receptor results in prolonged serum half-life. Thus, in some embodiments, a suitable Fc domain comprises one or more amino acid mutations that lead to improved binding to FcRn. Various mutations within the Fc domain that effect improved binding to FcRn are known in the art and can be adapted to practice the present invention. In some embodiments, a suitable Fc domain comprises one or more mutations at one or more positions corresponding to Thr 250, Met 252, Ser 254, Thr 256, Thr 307, Glu 380, Met 428, His 433, and/or Asn 434 of human IgG1.

In some embodiments, an anti-FLT-1 antibody or antigen binding fragment contains a spacer and/or is linked to another entity. In some embodiments, the linker or spacer comprises a sequence at least 50% (e.g., at least 55%, 60%, 65%, 70%, 75%, 80%, 85%, 90%, 95%, 96%, 97%, 98%, 99%, or 100%) identical to GAPGGGGGAAAAAGGGGG GAP (SEQ ID NO: 1) (GAG linker). In some embodiments, the linker or spacer comprises a sequence at least 50% (e.g., at least 55%, 60%, 65%, 70%, 75%, 80%, 85%, 90%, 95%, 96%, 97%, 98%, 99%, or 100%) identical to GAPGGGGGAAAAAGGGGG GAPGGGGGAAAAAGGGGGGAP (SEQ ID NO: 2) (GAG2 linker). In some embodiments, the linker or spacer comprises a sequence at least 50% (e.g., at least 55%, 60%, 65%, 70%, 75%, 80%, 85%, 90%, 95%, 96%, 97%, 98%, 99%, or 100%) identical to <u>GAPGGGGGAAAAGGGGG</u>
<u>GAPGGGGGAAAAGGGGG</u>
<u>GAPGGGGGAAAAGGGGG</u> <u>GAP</u> (SEQ ID NO: 3)
(GAG3 linker).

Production of Anti-Flt-1 Antibodies and Antigen Binding Fragments

A recombinant anti-Flt-1 antibody or antigen binding fragment suitable for the present invention may be produced by any available means. For example, a recombinant anti-Flt-1 antibody or antigen binding fragment may be recombinantly produced by utilizing a host cell system engineered to express a recombinant anti-Flt-1 antibody or antigen binding fragment-encoding nucleic acid.

Where antibodies are recombinantly produced, any expression system can be used. To give but a few examples, known expression systems include, for example, egg, baculovirus, plant, yeast, or mammalian cells.

In some embodiments, recombinant anti-Flt-1 antibody or antigen binding fragments suitable for the present invention are produced in mammalian cells. Non-limiting examples of mammalian cells that may be used in accordance with the present invention include BALB/c mouse myeloma line (NSO/1, ECACC No: 85110503); human retinoblasts (PER.C6, CruCell, Leiden, The Netherlands); monkey kidney CV1 line transformed by SV40 (COS-7, ATCC CRL 1651);

In some embodiments, the present invention provides recombinant anti-Flt-1 antibody or antigen binding fragment produced from human cells. In some embodiments, the present invention provides anti-Flt-1 antibody or antigen binding fragment produced from CHO cells.

Pharmaceutical Composition and Administration

The present invention further provides a pharmaceutical composition containing an anti-Flt-1 antibody or antigen binding fragment described herein and a physiologically acceptable carrier or excipient.

Suitable pharmaceutically acceptable carriers include but are not limited to water, salt solutions (e.g., NaCl), saline, buffered saline, alcohols, glycerol, ethanol, gum arabic, vegetable oils, benzyl alcohols, polyethylene glycols, gelatin, carbohydrates such as lactose, amylose or starch, sugars such as mannitol, sucrose, or others, dextrose, magnesium stearate, talc, silicic acid, viscous paraffin, perfume oil, fatty acid esters, hydroxymethylcellulose, polyvinyl pyrolidone, etc., as well as combinations thereof. The pharmaceutical preparations can, if desired, be mixed with auxiliary agents (e.g., lubricants, preservatives, stabilizers, wetting agents, emulsifiers, salts for influencing osmotic pressure, buffers, coloring, flavoring and/or aromatic substances and the like) which do not deleteriously react with the active compounds or interfere with their activity. In a preferred embodiment, a water-soluble carrier suitable for intravenous administration is used.

A suitable pharmaceutical composition or medicament, if desired, can also contain minor amounts of wetting or emulsifying agents, or pH buffering agents. A composition can be a liquid solution, suspension, emulsion, tablet, pill, capsule, sustained release formulation, or powder. A composition can also be formulated as a suppository, with traditional binders and carriers such as triglycerides. Oral formulations can include standard carriers such as pharmaceutical grades of mannitol, lactose, starch, magnesium stearate, polyvinyl pyrollidone, sodium saccharine, cellulose, magnesium carbonate, etc.

A pharmaceutical composition or medicament can be formulated in accordance with the routine procedures as a pharmaceutical composition adapted for administration to human beings. For example, in some embodiments, a composition for intravenous administration typically is a solution in sterile isotonic aqueous buffer. Where necessary, the composition may also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where the composition is to be administered by infusion, it can be dispensed with an infusion bottle containing sterile pharmaceutical grade water, saline or dextrose/water. Where the composition is administered by injection, an ampule of sterile water for injection or saline can be provided so that the ingredients may be mixed prior to administration.

Routes of Administration

An anti-Flt-1 antibody or antigen binding fragment described herein (or a composition or medicament containing an anti-Flt-1 antibody or antigen binding fragment described herein) is administered by any appropriate route. In some embodiments, an anti-Flt-1 antibody or antigen binding fragment protein or a pharmaceutical composition containing the same is administered parenterally. Parenteral administration may be intravenous, intradermal, intrathecal, inhalation, transdermal (topical), intraocular, intramuscular, subcutaneous, intramuscular, and/or transmucosal administration. In some embodiments, an anti-Flt-1 antibody or antigen binding fragment or a pharmaceutical composition containing the same is administered subcutaneously. As used herein, the term "subcutaneous tissue", is defined as a layer of loose, irregular connective tissue immediately beneath the skin. For example, the subcutaneous administration may be performed by injecting a composition into areas including, but not limited to, the thigh region, abdominal region, gluteal region, or scapular region. In some embodiments, an anti-Flt-1 antibody or antigen binding fragment thereof or a pharmaceutical composition containing the same is administered intravenously. In some embodiments, an anti-Flt-1 antibody or antigen binding fragment or a pharmaceutical composition containing the same is administered orally. More than one route can be used concurrently, if desired.

In some embodiments, administration results only in a localized effect in an individual, while in other embodiments, administration results in effects throughout multiple portions of an individual, for example, systemic effects. Typically, administration results in delivery of an anti-Flt-1 antibody or antigen binding fragment to one or more target tissues including but not limited to kidney, liver, brain, spinal cord, intestinal tract, eye, lung, spleen, heart, striated muscle, and smooth muscle.

In some embodiments, striated muscle is selected from the group consisting of triceps, tibialis anterior, soleus, gastrocnemius, quadriceps, and diaphragm.

In some embodiments, smooth muscle is selected from the group consisting of

Dosage Forms and Dosing Regimen

In some embodiments, a composition is administered in a therapeutically effective amount and/or according to a dosing regimen that is correlated with a particular desired outcome (e.g., with treating or reducing risk for a muscular dystrophy, such as Duchenne muscular dystrophy).

Particular doses or amounts to be administered in accordance with the present invention may vary, for example, depending on the nature and/or extent of the desired outcome, on particulars of route and/or timing of administration, and/or on one or more characteristics (e.g., weight, age, personal history, genetic characteristic, lifestyle parameter, severity of cardiac defect and/or level of risk of cardiac defect, etc., or combinations thereof). Such doses or amounts can be determined by those of ordinary skill. In some embodiments, an appropriate dose or amount is determined in accordance with standard clinical techniques. Alternatively or additionally, in some embodiments, an appropriate dose or amount is determined through use of one or more in vitro or in vivo assays to help identify desirable or optimal dosage ranges or amounts to be administered.

In various embodiments, an anti-Flt-1 antibody or antigen binding fragment thereof is administered at a therapeutically effective amount. Generally, a therapeutically effective amount is sufficient to achieve a meaningful benefit to the subject (e.g., treating, modulating, curing, preventing and/or ameliorating the underlying disease or condition). In some particular embodiments, appropriate doses or amounts to be administered may be extrapolated from dose-response curves derived from in vitro or animal model test systems.

In some embodiments, a provided composition is provided as a pharmaceutical formulation. In some embodiments, a pharmaceutical formulation is or comprises a unit dose amount for administration in accordance with a dosing regimen correlated with achievement of the reduced incidence or risk of a muscular dystrophy, such as Duchenne muscular dystrophy.

In some embodiments, a formulation comprising an anti-Flt-1 antibody or antigen binding fragment described herein administered as a single dose. In some embodiments, a formulation comprising an anti-Flt-1 antibody or antigen binding fragment described herein is administered at regular intervals. Administration at an "interval," as used herein, indicates that the therapeutically effective amount is administered periodically (as distinguished from a one-time dose). The interval can be determined by standard clinical techniques. In some embodiments, a formulation comprising an anti-Flt-1 antibody or antigen binding fragment described herein is administered bimonthly, monthly, twice monthly, triweekly, biweekly, weekly, twice weekly, thrice weekly, daily, twice daily, or every six hours. The administration interval for a single individual need not be a fixed interval, but can be varied over time, depending on the needs of the individual.

As used herein, the term "bimonthly" means administration once per two months (i.e., once every two months); the term "monthly" means administration once per month; the term "triweekly" means administration once per three weeks (i.e., once every three weeks); the term "biweekly" means administration once per two weeks (i.e., once every two weeks); the term "weekly" means administration once per week; and the term "daily" means administration once per day.

In some embodiments, a formulation comprising an anti-Flt-1 antibody or antigen binding fragment described herein is administered at regular intervals indefinitely. In some embodiments, a formulation comprising an anti-Flt-1 antibody or antigen binding fragment described herein is administered at regular intervals for a defined period.

In some embodiments, administration of an anti-Flt-1 antibody, or an antigen binding fragment thereof reduces the intensity, severity, or frequency, or delays the onset of at least one DMD sign or symptom. In some embodiments administration of an anti-Flt-1 antibody, or an antigen binding fragment thereof reduces the intensity, severity, or frequency, or delays the onset of at least one DMD sign or symptom selected from the group consisting of muscle wasting, skeletal deformation, cardiomyopathy, muscle ischemia, cognitive impairment, and impaired respiratory function.

In some embodiments, administration of an anti-Flt-1 antibody, or antigen binding fragment thereof improves clinical outcome as measured by a 6 minute walk test, quantitative muscle strength test, timed motor performance test. Brooke and Vignos limb function scales, pulmonary function test (forced vital capacity, forced expiratory volume in 1 second, peak expiratory flow rate, maximal inspiratory and expiratory pressures), health-related quality of life, knee and elbow flexors, elbow extensors, shoulder abduction, grip strength, time to rise from supine position, North Start Ambulatory Assessment, timed 10 meter walk/run, Egen-Klassification scale, Gowers score, Hammersmith motor ability, hand held myometry, range of motion, goniometry, hypercapnia, Nayley Scales of Infant and Toddler Development, and/or a caregiver burden scale.

Combination Therapy

In some embodiments, an anti-Flt-1 antibody or antigen binding fragment is administered in combination with one or more known therapeutic agents (e.g., corticosteroids) currently used for treatment of a muscular dystrophy. In some embodiments, the known therapeutic agent(s) is/are administered according to its standard or approved dosing regimen and/or schedule. In some embodiments, the known therapeutic agent(s) is/are administered according to a regimen that is altered as compared with its standard or approved dosing regimen and/or schedule. In some embodiments, such an altered regimen differs from the standard or approved dosing regimen in that one or more unit doses is altered (e.g., reduced or increased) in amount, and/or in that dosing is altered in frequency (e.g., in that one or more intervals between unit doses is expanded, resulting in lower frequency, or is reduced, resulting in higher frequency).

EXAMPLES

Example 1. Generation and Characterization of High Affinity Anti-Flt-1 Antibodies Antibody 01A04

Figure 2:
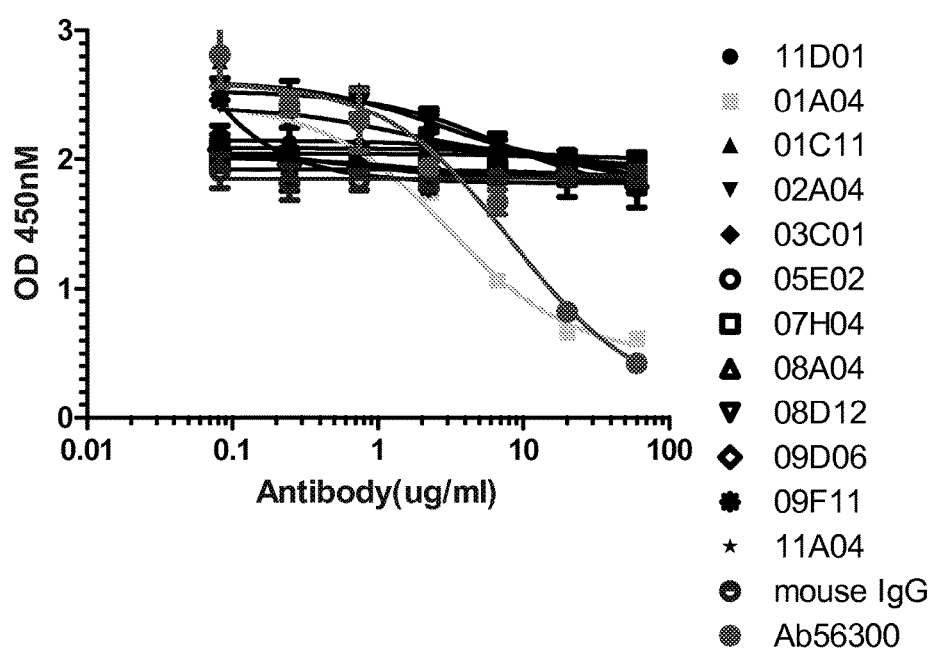
FIG. 2 shows exemplary results illustrating competitive binding of monoclonal antibodies with human soluble Flt-1 in an ELISA. A competition ELISA of hybridoma supernatants for VEGF binding on human Flt-1 is depicted. The negative control (purified polyclonal mouse IgG) does not show any competition on human Flt-1, while fusion product 01A04 and positive control commercial antibody Abcam56300 are competitive binders.

An antibody was generated against soluble Flt-1 using traditional mouse monoclonal antibody methodology. Briefly, Balb/c mice were immunized with recombinant human soluble Flt-1 (purchased from ABCAM). On day 20 post-immunization, animals were titered for anti-sFlt-1 production by ELISA (FIG. 1). One mouse was found to be a high titer responder; this animal was subsequently boosted with antigen and sacrificed 5 days later. Spleen and lymph node cells from this animal were fused to mouse myeloma partners to produce hybridomas. Hybridoma supernatants were screened versus sFlt-1 antigen, and positive responders were scaled up and re-assayed for binding to both human and mouse sFlt-1, as well as the ability to compete with sFlt-1 for VEGF binding. There were no cross reactive hybridomas that could bind to both human and mouse sFlt-1. However, among human sFlt-1 reactive hybridomas, several sFlt-1:VEGF antagonists were identified by competition ELISA (see FIG. 2 for a representative experiment). The most potent of these, fusion partner 01A04, was subjected to three rounds of single cell cloning to achieve monoclonal antibody 01A04. This antibody was further characterized for binding affinity to sFlt-1 antigen (ELISA, BIACORE and FACs); IC50 in sFlt-1:VEGF competition ELISA; and performance in cell based assays.

Antibody 01A04 Characterization—Binding

Figure 3:
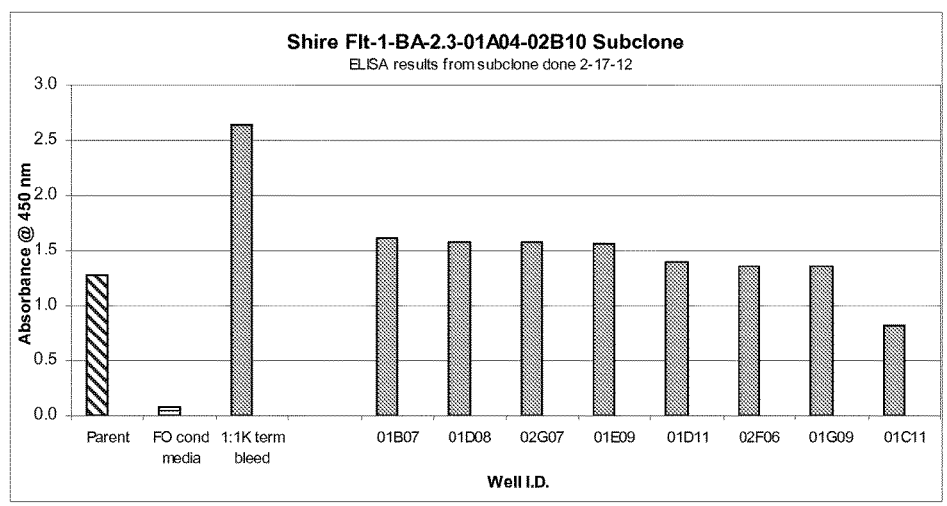
FIG. 3 shows exemplary monoclonal antibody binding to soluble human Flt-1. Direct binding ELISA of purified IgG from hybridoma clone 01A04-02B10 sub-clones versus human sFlt-1 antigen is depicted. Based upon absorbance readings and microscopic morphology, sub-clone 01A04-02B10-02G07 was chosen for further scale up and characterization.
Figure 4:
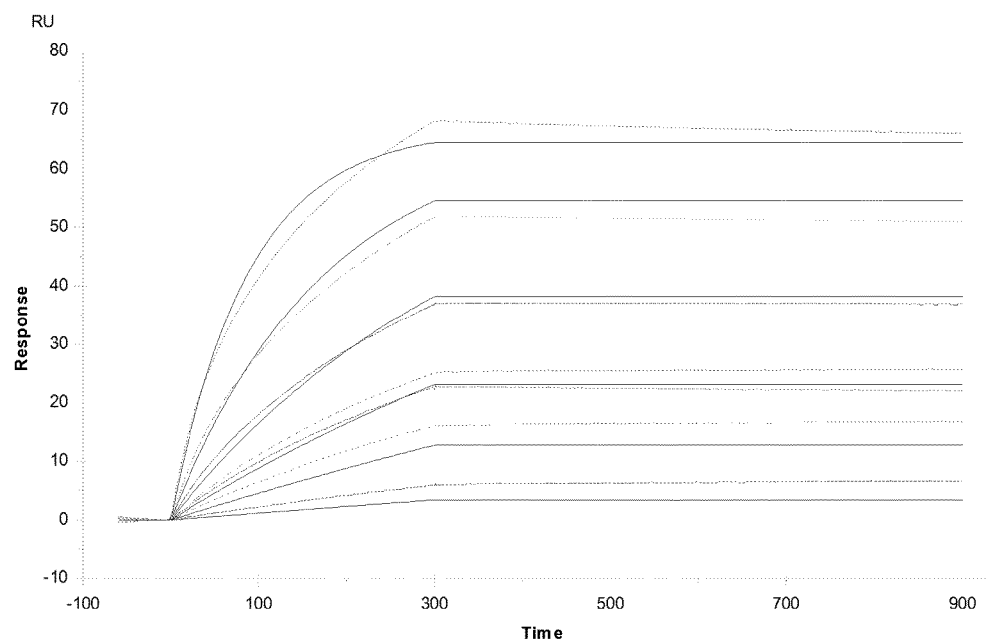
FIG. 4 shows exemplary results illustrating monoclonal antibody binding to soluble human Flt-1 via surface plasmon resonance (BIACORE) assay. Surface plasmon resonance sensograms for hybridoma clone 01A04 (sub-clone 02B10-02G07) IgG binding to immobilized human sFlt-1 antigen is depicted.

Following cloning and sub-cloning of the fusion partner parent, multiple sub-clones of the 01A04 parent demonstrated binding to immobilized soluble Flt-1 (FIG. 3). One of these subclones, monoclonal 01A04-02B10-02G07 was chosen for scale up and cell banking based upon antigen binding, clone morphology and viability. The binding constant of 01A04-02B10-02G07 for sFlt-1 antigen was determined via surface plasmon resonance methodology (BIACORE, see FIG. 4). Monoclonal antibody 01A04-02B10-02G07 is a sub-nanomolar binder to human sFlt-1.

Antibody 01A04 Characterization—Cross-Reactivity

Figure 5:
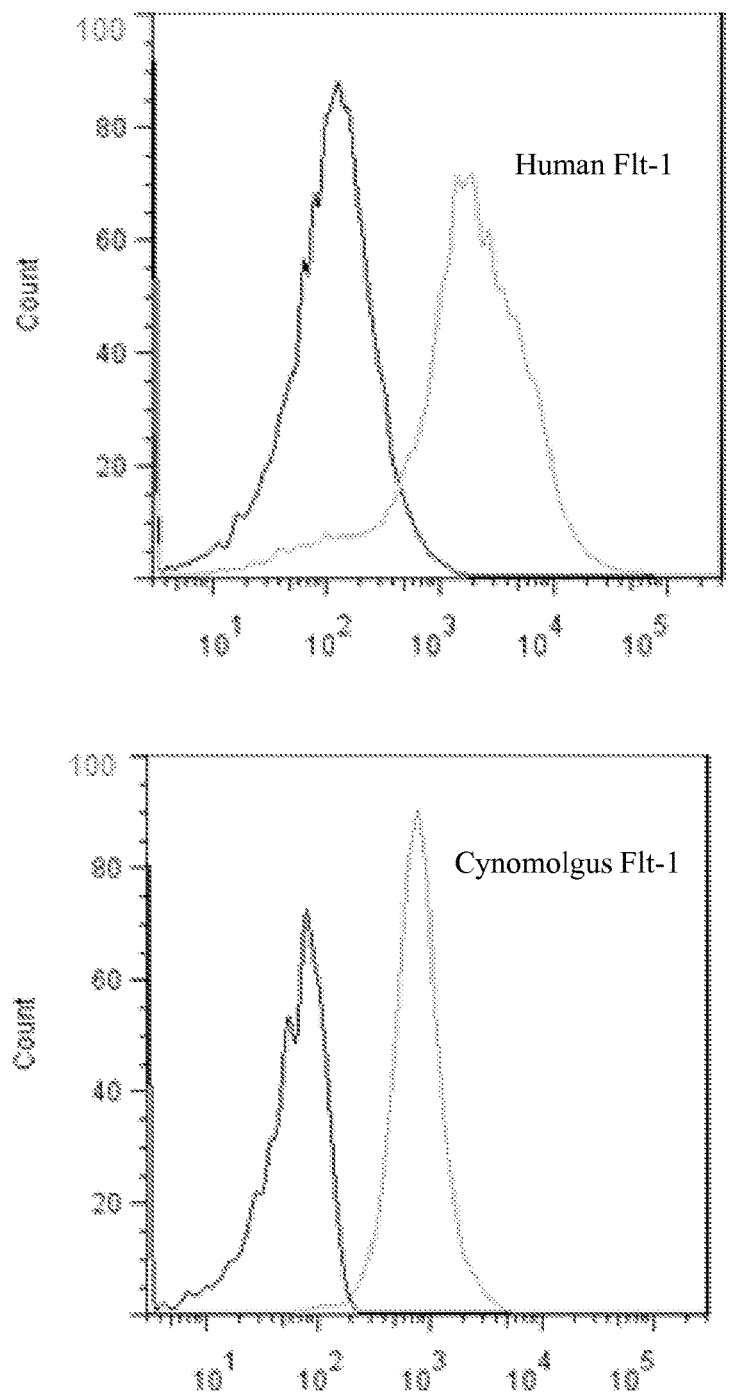
FIG. 5 shows exemplary results illustrating cross-reactivity of monoclonal antibody binding with cyno (monkey) Flt-1. Binding of purified IgG from hybridoma clone 01A04 (sub-clone 02B10-02G07) to cell lines over-expressing human and cynomolgus Flt-1 is depicted. The darker histogram represents an isotype control antibody. The lighter histogram represents monoclonal antibody 01A04-02B10-02G7.

Binding of monoclonal antibody 01A04 to the Flt-1 receptor expressed on cells was tested with FACS. Three transfected cell lines were tested expressing human, mouse or cyno Flt-1. Binding to all three cell lines was tested by incubating the cells with antibody for one hour. Binding of the antibody to the cells was then revealed with an anti-mouse IgG PE antibody. Results are shown in FIG. 5. Consistent with ELISA and BIACORE data, monoclonal antibody 01A04 does not bind to mouse Flt-1. However, the antibody does bind to human and cynomolgus Flt-1 expressed on cells.

Antibody 01A04 Characterization—Competition

Figure 6:
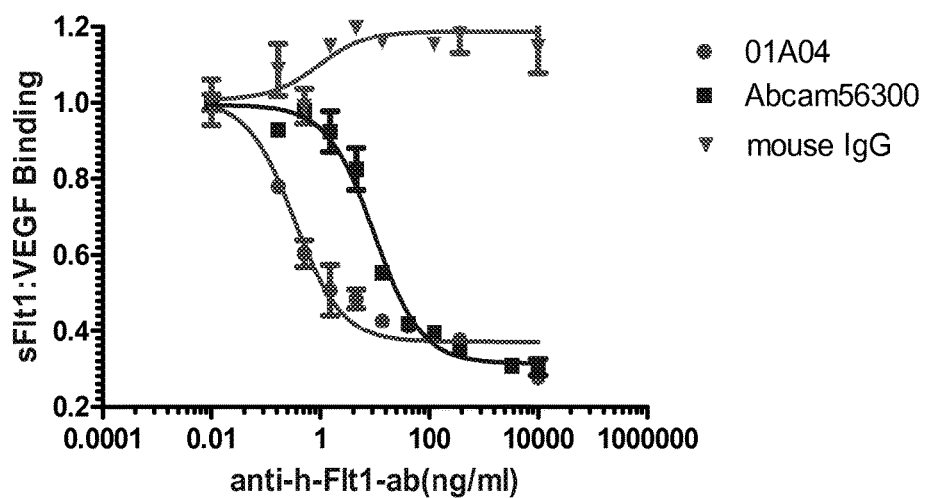
FIG. 6 shows exemplary results illustrating competitive binding of monoclonal antibodies with human soluble Flt-1 in an ELISA. VEGF:sFlt-1 $IC_{50}$ determination of monoclonal antibody 01A04 (sub-clone 02B10-02G07) versus a commercial benchmark is depicted. Values were obtained by performing competition ELISA of the respective IgGs for VEGF binding on human Flt-1. The negative control (purified polyclonal mouse IgG) does not show any competition on human Flt-1 while monoclonal antibody 01A04, and commercial anti-sFlt-1 antibody from Abcam (catalog number 56300), compete for the VEGF binding site. Monoclonal antibody 01A04 is a more potent antagonist than the commercial benchmark. The $IC_{50}$ for 01A04 was 2.3 pM. The $IC_{50}$ for ABcam 56300 was 65 pM.

To estimate the potency of the antibodies, the competition ELISA (using human sFlt-1 and VEGF) that was set-up for the screening of the llama Fabs and IgGs was used. A concentration range from 10 to 0.01 µg/ml of IgG was tested. Monoclonal antibody 01A04 was assayed versus both negative control (purified polyclonal mouse IgG) and positive control (commercial anti-sFlt-1 monoclonal antibody Abcam56300) molecules. Half maximal inhibition (IC50) values were calculated. Results are presented in FIG. 6.

Antibody 01A04 Characterization—Cell Based Assay

Figure 7:
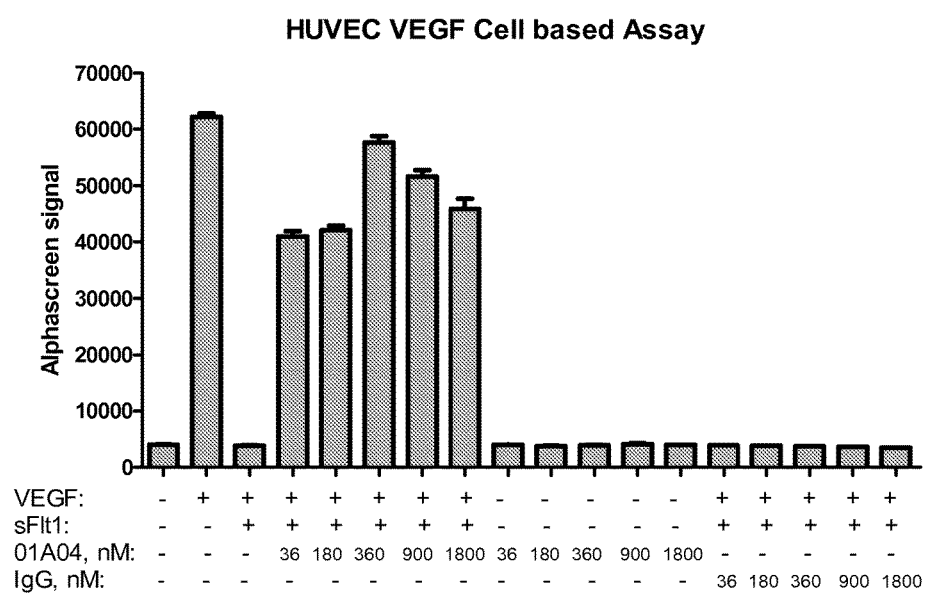
FIG. 7 shows exemplary results illustrating anti-Flt-1 monoclonal antibody inhibition of VEGF binding to sFlt-1 in a cell based assay. Primary HUVECs were treated with recombinant human VEGF (100 ng/mL, 2.4 nM) in the presence or absence of recombinant human soluble Flt-1 (15× molar equivalent, 36 nM) and monoclonal antibody 01A04 (sub-clone 02B10-02G07). Addition of 01A04 rescues VEGF induced HUVEC activation, as measured by phosphorylation of the cytoplasmic tail of VEGF R2. Monoclonal antibody 01A04 alone has no effect on receptor phosphorylation, while control IgG is unable to rescue signaling in the presence of VEGF and soluble Flt-1.

Human primary umbilical vein endothelial cells (HUVECs) were stimulated with VEGF in the presence or absence of soluble Flt-1 and monoclonal antibody 01A04. VEGF induced activation of cells was assayed by determining the phosphorylation status of the VEGF R2 receptor. In the presence of soluble Flt-1, VEGF induced HUVEC activation is attenuated. Addition of monoclonal antibody 01A04 rescues cell activation by antagonizing soluble Flt-1 (FIG. 7).

Example 2. In Vivo Efficacy of Anti-Flt-1 Antibody

Administration of Anti-Flt-1 Antibody into Mdx Mice

Mice (n=8) were injected with anti-Flt-1 antibody (0 (PBS), 0.1 mg, or 0.5 mg, i.v.) beginning at postnatal day 21. Anti-Flt-1 antibody was sourced from a commercial vendor (Angio Proteomie, catalog number AP-MAB0702). This antibody is a known Flt-1:VEGF antagonist. Mice received injections every 3 days until day 48. On day 53, in vivo effects were assessed. In a second set of experiments, antibody performance was tested against an isotype matched control antibody which does not bind Flt1. Mice received injections twice weekly at a fixed dose of 20 mg/kg from day 28 until day 56. On day 57, in vivo effects were assessed.

Histopathology

Figure 8:
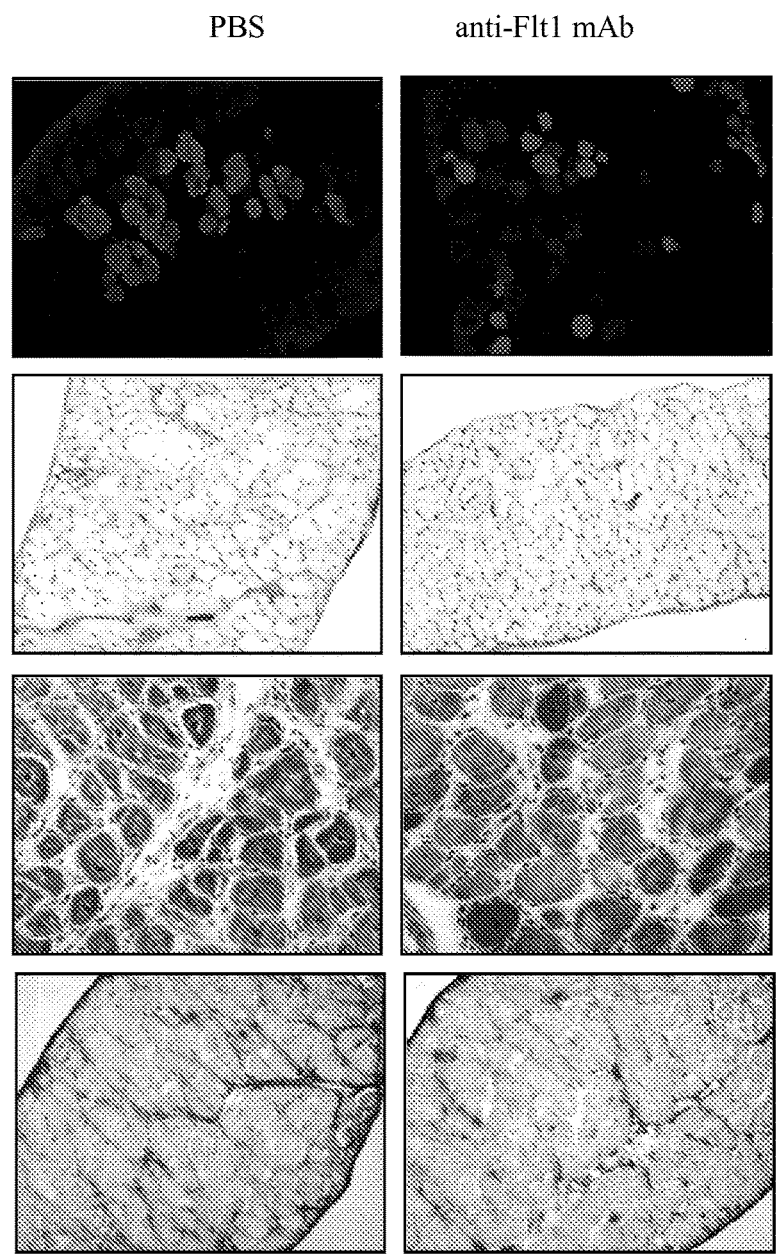
FIG. 8 shows exemplary photomicrographs illustrating improved muscle histopathology by administration of an anti-Flt-1 antibody. Improvement in mdx muscle pathology following treatment with anti-sFlt-1 monoclonal antibody is depicted. Animals were treated with commercial monoclonal antibody to sFlt-1 (Angio Proteomie, clone AP-MAB0702) or PBS as control. The top row shows Evans blue dye staining of diaphragm muscle. The second row shows CD31 staining of diaphragm muscle to quantify blood vessels. The third row shows H+E staining of diaphragm muscle. The bottom row shows Van Giesson staining of diaphragm muscle to quantify fibrosis.
Figure 9:
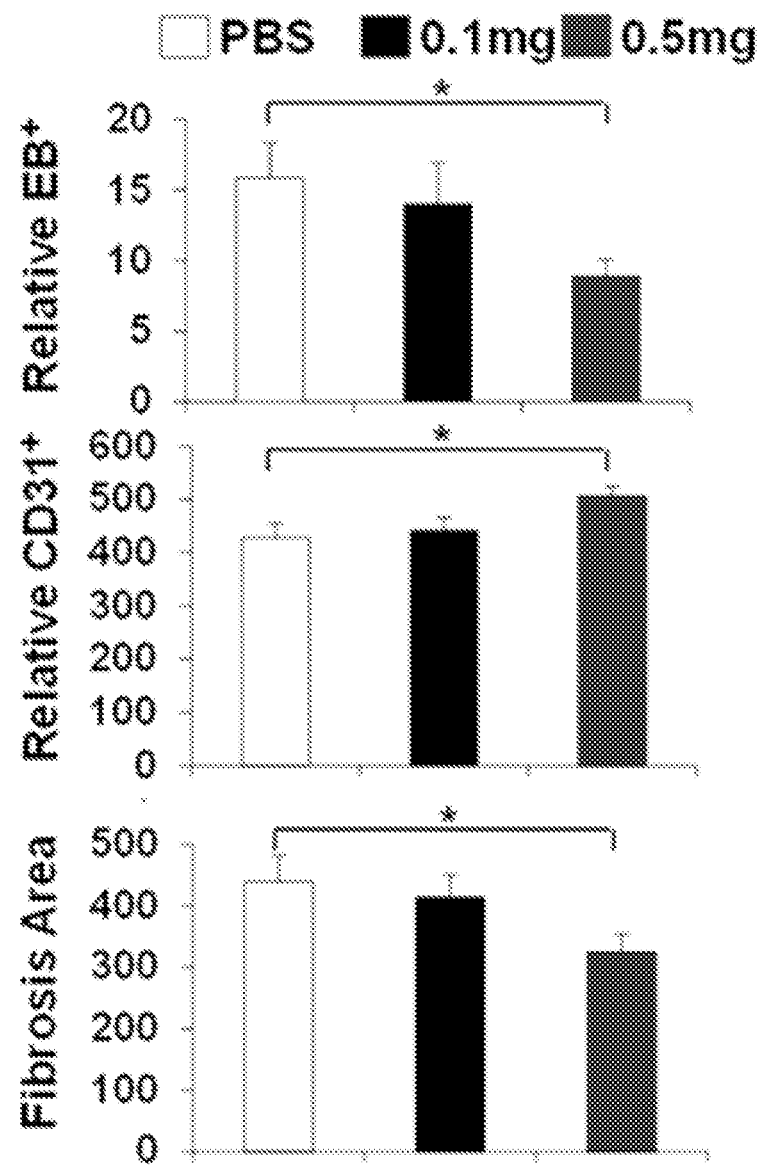
FIG. 9 shows exemplary results illustrating quantification of histopathological markers indicating improved muscle histology by administration of an anti-Flt-1 antibody to mice. Quantification of histopathology data presented in FIG. 8 is depicted. The number of Evans blue positive fibers (top panel), CD31+ blood vessels (second panel); and centrally located nuclei (third panel) were manually counted under 4× and 10× magnification. Total fibrotic area was quantified using image analysis software (bottom panel). *=$p<0.05$ by student's unpaired t-test.
Figure 10:
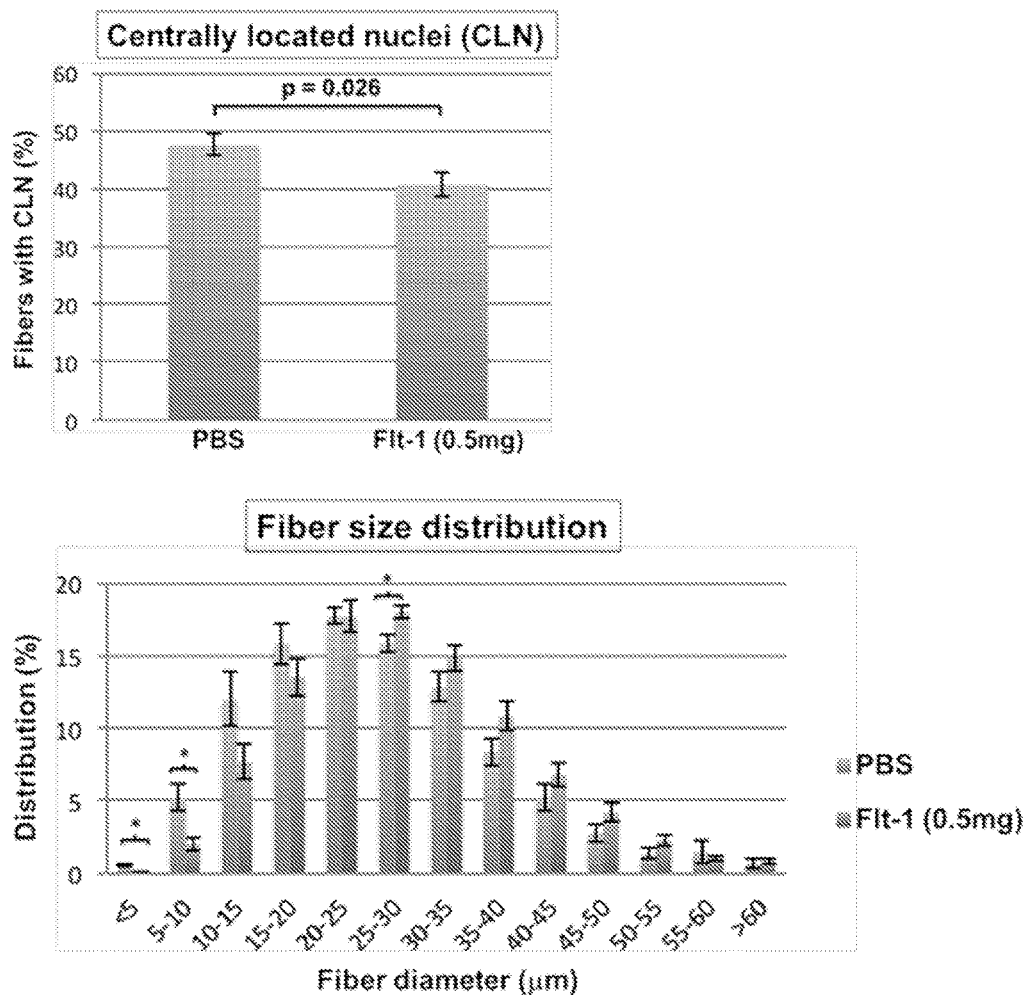
FIG. 10 shows exemplary results illustrating quantification of histopathological markers indicating improved muscle histology by administration of an anti-Flt-1 antibody to mice. Quantification of histopathology data presented in FIG. 8 is depicted. Top: Reduced fibers with centrally located nuclei (CLN) in diaphragm following treatment with anti-Flt1 monoclonal antibody. Fibers with CLN were manually counted under 4× and 10× magnification. Bottom: Slight shift to larger fiber size in diaphragm following treatment with anti-Flt1 monoclonal antibody. Fiber diameters were manually counted under 4× and 10× magnification. *=p<0.05 by student's unpaired t-test.
Figure 12:
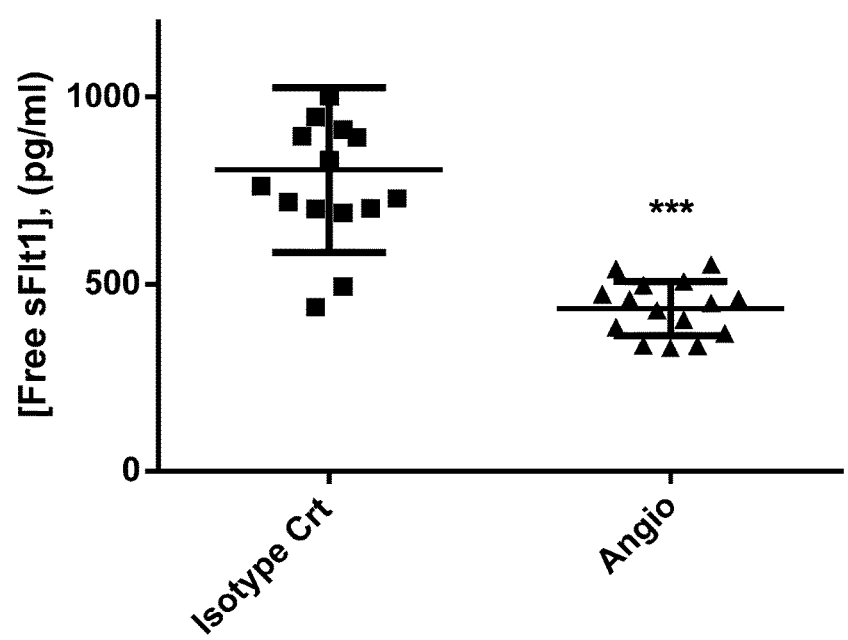
FIG. 12 shows exemplary results illustrating in vivo reduction of free soluble Flt1 in the serum. Administration of an Flt-1 antibody to mdx mice caused a highly significant reduction in the levels of soluble Flt1 in the blood as compared to an isotype control antibody. Animals were dosed at 20 mg/kg twice weekly for four weeks beginning at 4 weeks of age. At necropsy, blood was collected for biomarker analysis. *** p<0.001 versus isotype.
Figure 13:
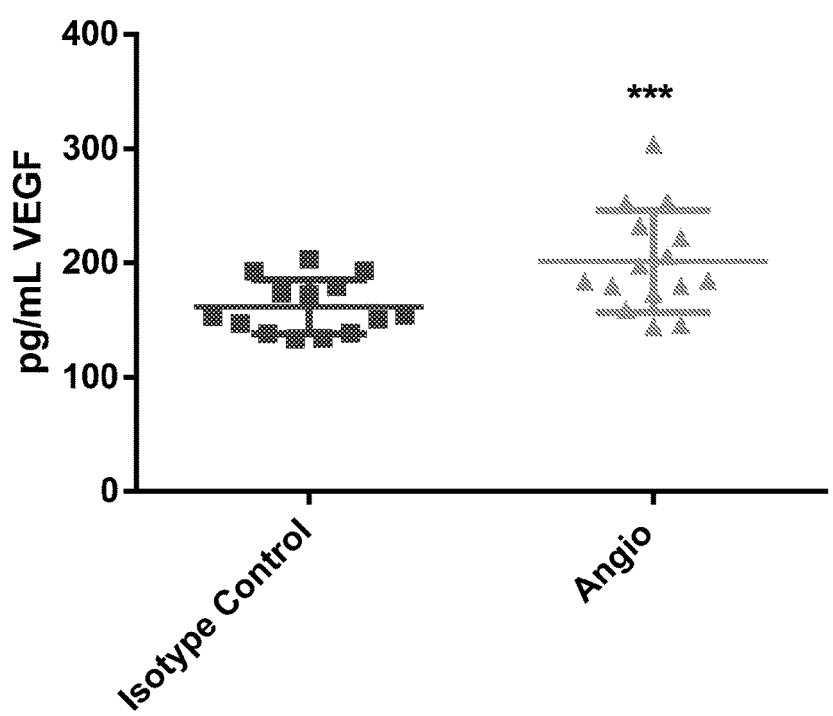
FIG. 13 shows exemplary results illustrating in vivo increases in the serum VEGF concentration. Administration of an Flt-1 antibody to mdx mice caused a highly significant increase in the levels of free VEGF in the blood as compared to an isotype control antibody. Animals were dosed at 20 mg/kg twice weekly for four weeks beginning at 4 weeks of age. At necropsy, blood was collected for biomarker analysis. *** p=0.0063 versus isotype.
Figure 14:
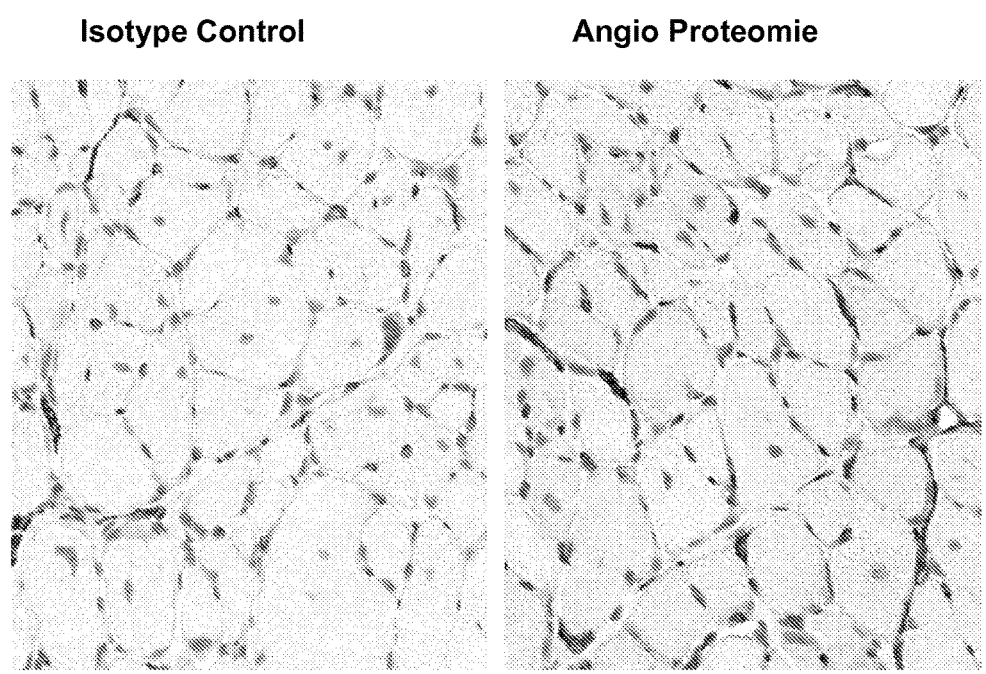
FIG. 14 shows exemplary results illustrating in vivo increases in angiogenesis in the diaphragm muscle. Administration of an Flt-1 antibody to mdx mice caused a significant increase in endothelial cell proliferation, as exemplified by CD31 staining, in the diaphragm muscle as compared to an isotype control antibody. Animals were dosed at 20 mg/kg twice weekly for four weeks beginning at 4 weeks of age. At necropsy, tissues were preserved for histapthology. Depicted is staining for CD31, an endothelial cell marker. There was a statistically significant increase (p<0.05) in endothelial cell number following treatment with anti-Flt-1 monoclonal antibody. Data were analyzed using automated quantitative imaging software. Samples were blinded to the investigator.

Treatment with an anti-Flt-1 antibody at a dose of 0.5 mg (i.v.) significantly improved muscle pathology in mdx mice as compared to vehicle control (FIGS. 8, 9 and 10). Specifically, muscle fiber integrity was improved, as determined by decreased Evan's blue dye accumulation in the diaphragm muscle (FIG. 8, upper panel); fibrosis was decreased, as determined by van Giesson staining of the diaphragm muscle (FIG. 8, lower panel); and muscle necrosis was decreased, as determined by hematoxylin and eosin (H+E) staining of the diaphragm muscle (FIG. 8, third panel from the top). Centrally located nuclei (CLN) in muscle fibers are a typical phenotype associated with DMD. Lower CLN in the antibody-treated group is indicative of the decreased fiber turnover and increased muscle fiber stability (FIG. 10). Increased muscle health is hypothesized to occur due to increased muscle perfusion, as antibody treated animals displayed increased numbers of CD31+ blood vessels in diaphragm and tibialis anterior muscles (FIG. 8, second panel; FIG. 14). Results are quantified in FIGS. 9,10 and 14. Proliferation of CD31+ blood vessel cells is further hypothesized to result from the neutralization of the endogenous VEGF antagonist soluble Flt1 (FIG. 12), leading to increased free VEGF in the bloodstream of the treated mice (FIG. 13).

Muscle Function

Figure 11:
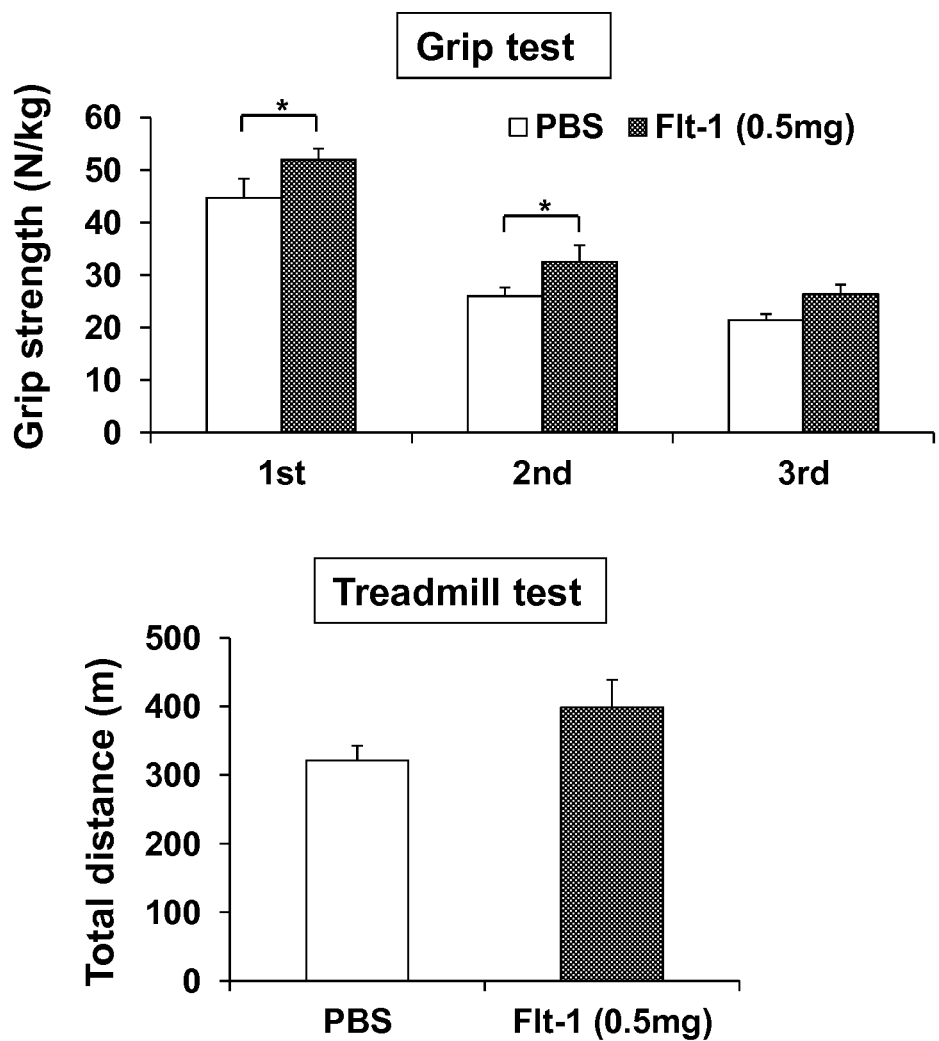
FIG. 11 shows exemplary results illustrating in vivo efficacy of Flt-1 antibody on muscle function. Administration of an Flt-1 antibody to mdx mice improved performance on grip test (upper panel) and treadmill test (lower panel) as compared to control mdx mice administered PBS. Animal grip strength was measured three independent times per animal, with 30 minutes separating each trial. Total treadmill distance was measured 3 times per animal.

Treatment with an anti-Flt-1 antibody at a dose of 0.5 mg (i.v.) significantly improved muscle function in mice in a grip test (FIG. 1, upper panel) and showed a clear trend for improvement in a treadmill test (FIG. 11, lower panel).

EQUIVALENTS AND SCOPE

Those skilled in the art will recognize, or be able to ascertain using no more than routine experimentation, many equivalents to the specific embodiments of the invention described herein. The scope of the present invention is not intended to be limited to the above Description, but rather is as set forth in the following claims.

We claim:

1. A method of treating Duchenne Muscular Dystrophy (DMD) comprising administering to an individual who is suffering from or susceptible to DMD an effective amount of an anti-Flt-1 monoclonal antibody, or an antigen binding fragment thereof, such that at least one symptom of DMD is reduced in intensity, severity, or frequency, or has delayed onset, and wherein the anti-Flt-1 monoclonal antibody, or antigen binding fragment thereof, inhibits binding of VEGF to Flt-1 receptor.

2. The method of claim 1, wherein the anti-Flt-1 monoclonal antibody, or an antigen binding fragment thereof, is selected from the group consisting of IgG, F(ab')$_2$, F(ab)$_2$, Fab', Fab, ScFvs, diabodies, triabodies and tetrabodies.

3. The method of claim 2, wherein the anti-Flt-1 monoclonal antibody, or an antigen binding fragment thereof, is IgG.

4. The method of claim 3, wherein the anti-Flt-1 monoclonal antibody, or an antigen binding fragment thereof, is a monoclonal antibody.

5. The method of claim 1, wherein the anti-Flt-1 monoclonal antibody, or an antigen binding fragment thereof, is administered parenterally.

6. The method of claim 1, wherein the anti-Flt-1 monoclonal antibody, or an antigen binding fragment thereof, is delivered to one or more skeletal muscles selected from orbicularis oculi, ciliary, iris dilator, iris sphincter, auriculares, temporoparietalis, stapedius, tensor tympani, procerus, nasalis, dilator naris, depressor septi nasi, levator labii superioris alalaeque nasi, levator anguli oris, depressor anguli oris, orbicularis oris, buccinator zygomaticus major and minor, platysma, levator labii superioris, depressor labii inferioris, risorius, mentalis, corrugator supercilii, anconeus, pronator teres, supinator, brachialis, masseter, temporalis, medial pterygoid, lateral pterygoid, genioglossus, styloglossus, palatoglossus, hyoglossus, digastric, stylohoid, mylohyoid, geniohyoid, omohyoid, sternohyoid, sternothyrioid, thyrohyoid, sternocleidomastoid, anterior scalene, middle scalene, posterior scalene, subclavius, pectoralis major, pectoralis minor rectus abdominis, external abdominal oblique, internal abdominal oblique, transversus abdominis, diaphragm, external intercostals, internal intercostals, serratus anterior, trapezius, levator scapulae, rhomboideus major, rhomboideus minor, latissimus dorsi, deltoid, subscapularis, supraspinatus, infraspinatus, teres major, teres minor, coracobrachialis, biceps brachii-long head, biceps brachii-short head, triceps brachii-long head, triceps brachii-lateral head, triceps brachii-medial head, anconeus, pronator teres, supinator, brachialis, brachioradialis, flexor carpi radialis, flexor carpi ulnaris, palmaris longus, extensor carpi ulnaris, ulnaris, extensor carpi radialis longus, extensor carpi, radialis brevis, extensor digitorum, extensor digiti minimi, erector spinae: cervicalis, erector spinae: spinalis, erector spinae: longissimus, erector spinae:iliocostalis, thenar, abductor pollicis brevis, flexor pollicis brevis, opponens pollicis, hypothenar, abductor digiti minimi, flexor digiti minimi brevis, opponens digiti minimi, palmar interossei, dorsal interossei, lumbricals, iliopsoas: psoas major, iliopsoas: iliacus, quadratus femoris, adductor longus, adductor brevis, adductor magnus, gracilis, sartorius, quadriceps femoris: rectus femoris, quadriceps femoris: vastus lateralis, quadriceps femoris: vastus medialis, quadriceps femoris: vastus intermedius, gastrocnemius, fibularis (peroneus) longus, soleus, gluteus maximus, gluteus medius, gluteus minimus, hamstring: biceps, femoris: long head, hamstrings: biceps, femoris: short head, hamstrings: semitendinosus, hamstrings: semimembranosus, tensor fasciae latae, pectineus, tibialis anterior, extensor digitorum longus, extensor halluces longus, peroneus brevis, plantaris tibialis posterior, flexor halluces longus, extensor digitorum brevis, extensor halluces brevis, abductor halluces, flexor halluces brevis, abductor digiti minimi, flexor digiti minimi, opponens digiti minimi, extensor digitorum brevis, lumbricales of the foot, quadratus plantae, flexor accessories, flexor digitorum brevis, dorsal interossei, or plantar interossei.

7. The method of claim 1, wherein the administration of the anti-Flt-1 monoclonal antibody, or an antigen binding fragment thereof, results in muscle regeneration, fibrosis reduction, increased stability, increased muscle strength, increased flexibility, increased range of motion, increased stamina, reduced fatiguability, increased blood flow, improved cognition, improved pulmonary function, or inflammation inhibition.

\* \* \* \* \*